United States Patent
Tsubouchi et al.

(10) Patent No.: US 9,971,402 B2
(45) Date of Patent: May 15, 2018

(54) INFORMATION PROCESSING SYSTEM, MOBILE TERMINAL, SERVER APPARATUS, METHOD FOR PROCESSING INFORMATION, AND NON-TRANSITORY COMPUTER READABLE STORAGE MEDIUM

(71) Applicant: YAHOO JAPAN CORPORATION, Tokyo (JP)

(72) Inventors: Kota Tsubouchi, Tokyo (JP); Kentaro Nishi, Tokyo (JP)

(73) Assignee: YAHOO JAPAN CORPORATION, Tokyo (JP)

( * ) Notice: Subject to any disclaimer, the term of this patent is extended or adjusted under 35 U.S.C. 154(b) by 0 days. days.

(21) Appl. No.: 15/225,093

(22) Filed: Aug. 1, 2016

(65) Prior Publication Data
US 2017/0076578 A1 Mar. 16, 2017

(30) Foreign Application Priority Data
Sep. 16, 2015 (JP) ................................ 2015-183144

(51) Int. Cl.
| G02B 27/00 | (2006.01) |
| G06F 3/01 | (2006.01) |
| A61B 3/113 | (2006.01) |
| G06F 21/00 | (2013.01) |

(52) U.S. Cl.
CPC .............. G06F 3/013 (2013.01); A61B 3/113 (2013.01); G06F 3/011 (2013.01); G06F 3/012 (2013.01); G06F 21/00 (2013.01)

(58) Field of Classification Search
CPC ........................................................ G02B 27/00
USPC ..................................................... 340/539.13
See application file for complete search history.

(56) References Cited

U.S. PATENT DOCUMENTS

| 6,507,802 B1 * | 1/2003 | Payton .................... G06Q 99/00 702/150 |
| 2015/0087257 A1 * | 3/2015 | Balram .................... H04W 4/12 455/404.1 |
| 2016/0239080 A1 * | 8/2016 | Marcolina ............... G06F 3/011 |

FOREIGN PATENT DOCUMENTS

| JP | 2003-523581 A | 8/2003 |
| JP | 2007-133531 A | 5/2007 |
| JP | 2008-040758 A | 2/2008 |
| JP | 2015-191554 A | 11/2015 |

OTHER PUBLICATIONS

Mar. 21, 2017 Office Action issued in Japanese Patent Application No. 2015-183144.

* cited by examiner

*Primary Examiner* — Qutbuddin Ghulamali
(74) *Attorney, Agent, or Firm* — Oliff PLC

(57) ABSTRACT

An information processing system includes an acquiring unit that acquires motion information indicating a current motion of a user, a determining unit that compares the motion information acquired by the acquiring unit with standard information indicating a motion of the user in a predetermined state to determine the presence or absence of a state change of the user, and a calculating unit that, when the determining unit determines that a state change is present, calculates an area that the user visually recognizes based on sight line information concerning a sight line of the user contained in the motion information.

13 Claims, 17 Drawing Sheets

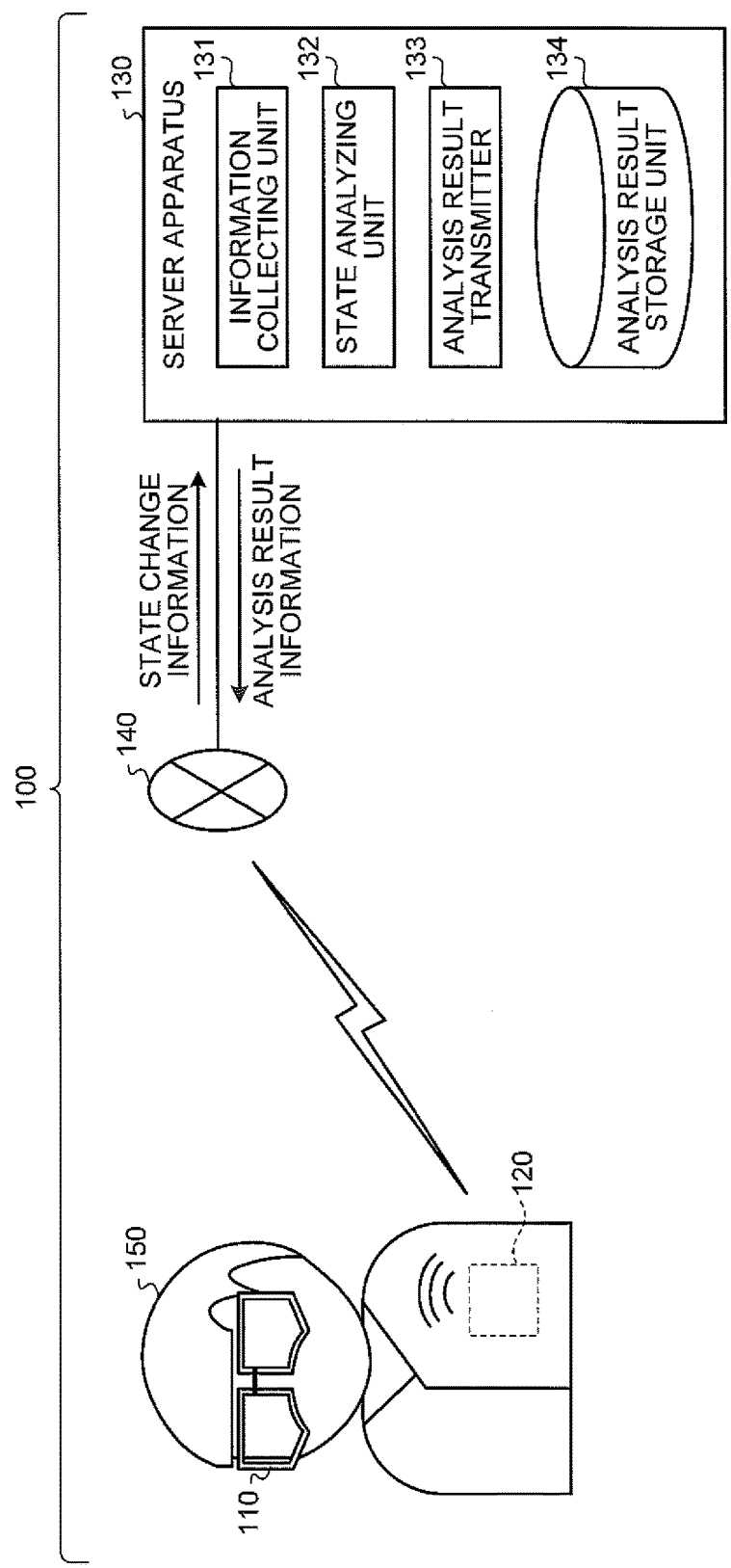

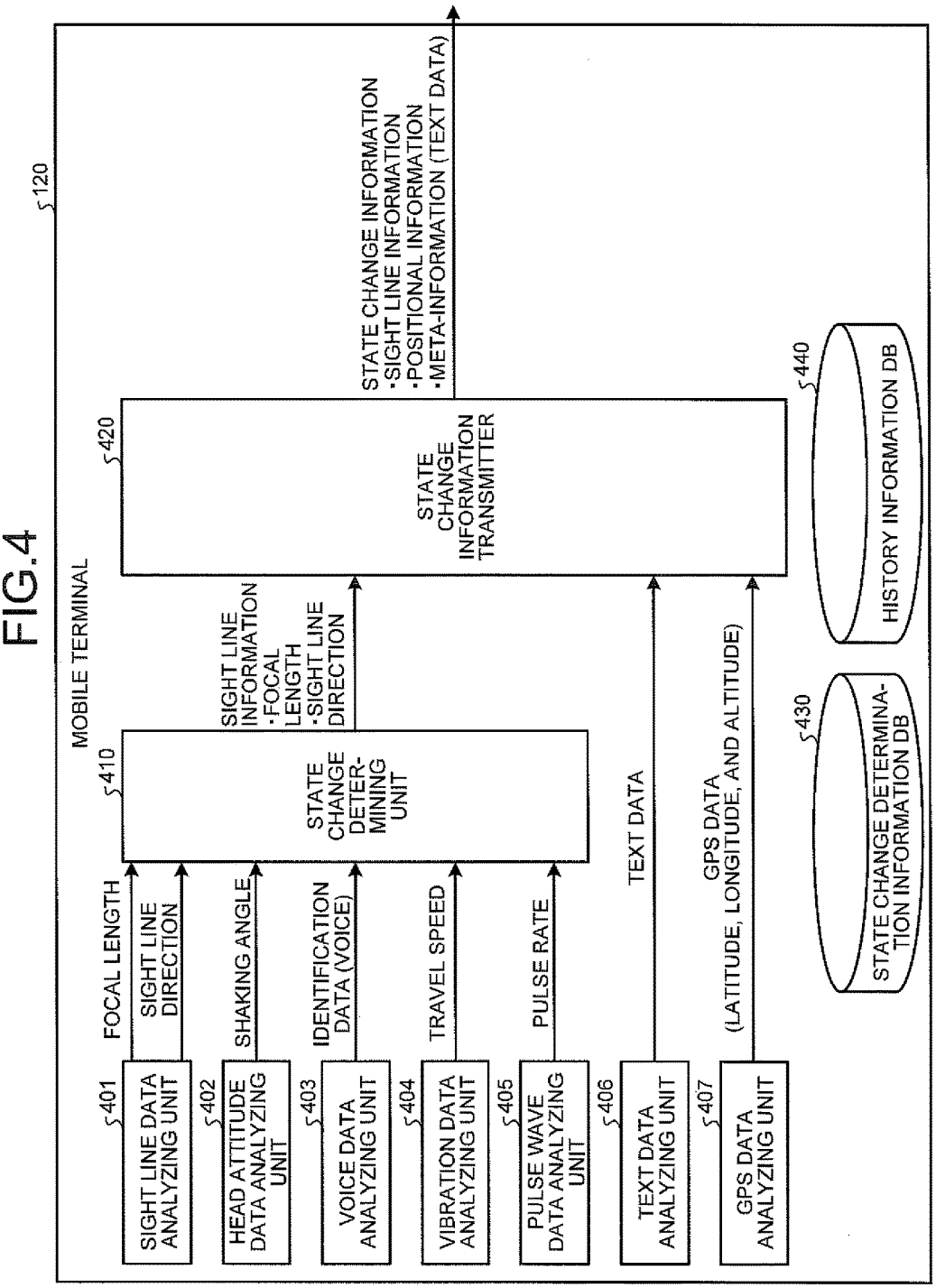

FIG.5

| STATE CHANGE DETERMINATION INFORMATION | |
|---|---|
| DETERMINATION DATA | STANDARD INFORMATION FOR DETERMINING THAT STATE OF USER IS NOT STATIONARY STATE |
| FOCAL LENGTH L | $L1 \leq L$ |
| TIME T DURING WHICH SIGHT LINE DIRECTION IS CONSTANT | $T1 \leq T$ |
| SHAKING ANGLES θ, φ | SIDE-TO-SIDE : $\theta \leq (-\theta1), (+\theta1) \leq \theta$<br>UP-AND-DOWN : $\phi \leq (-\phi1), (+\phi1) \leq \phi$ |
| TRAVEL SPEED V | $V = 0$ |
| IDENTIFICATION DATA (VOICE) | IDENTIFICATION DATA (VOICE) = "Whoops," "Look at that," ... |
| PULSE RATE P | $P2 \leq P$ |

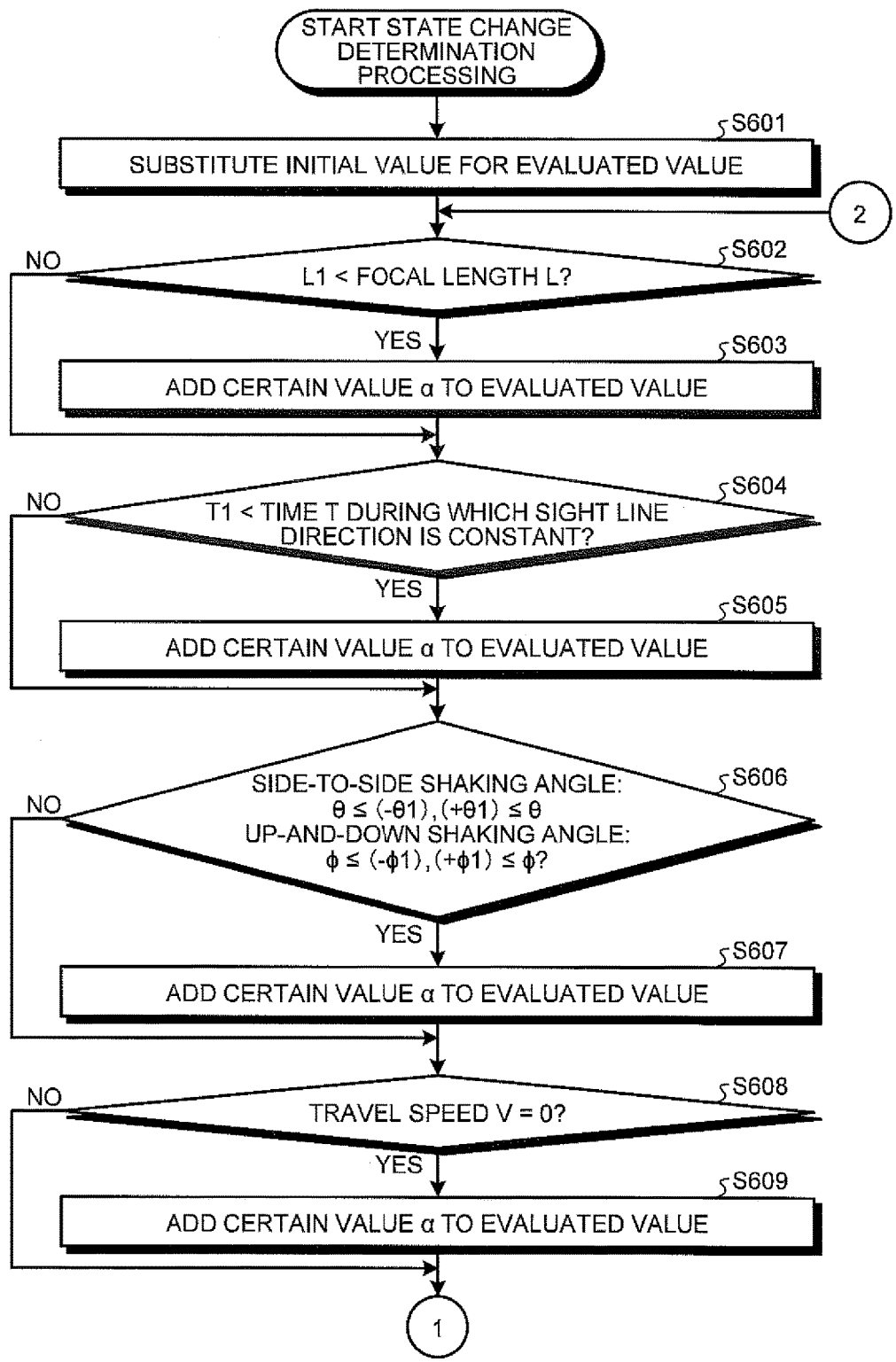

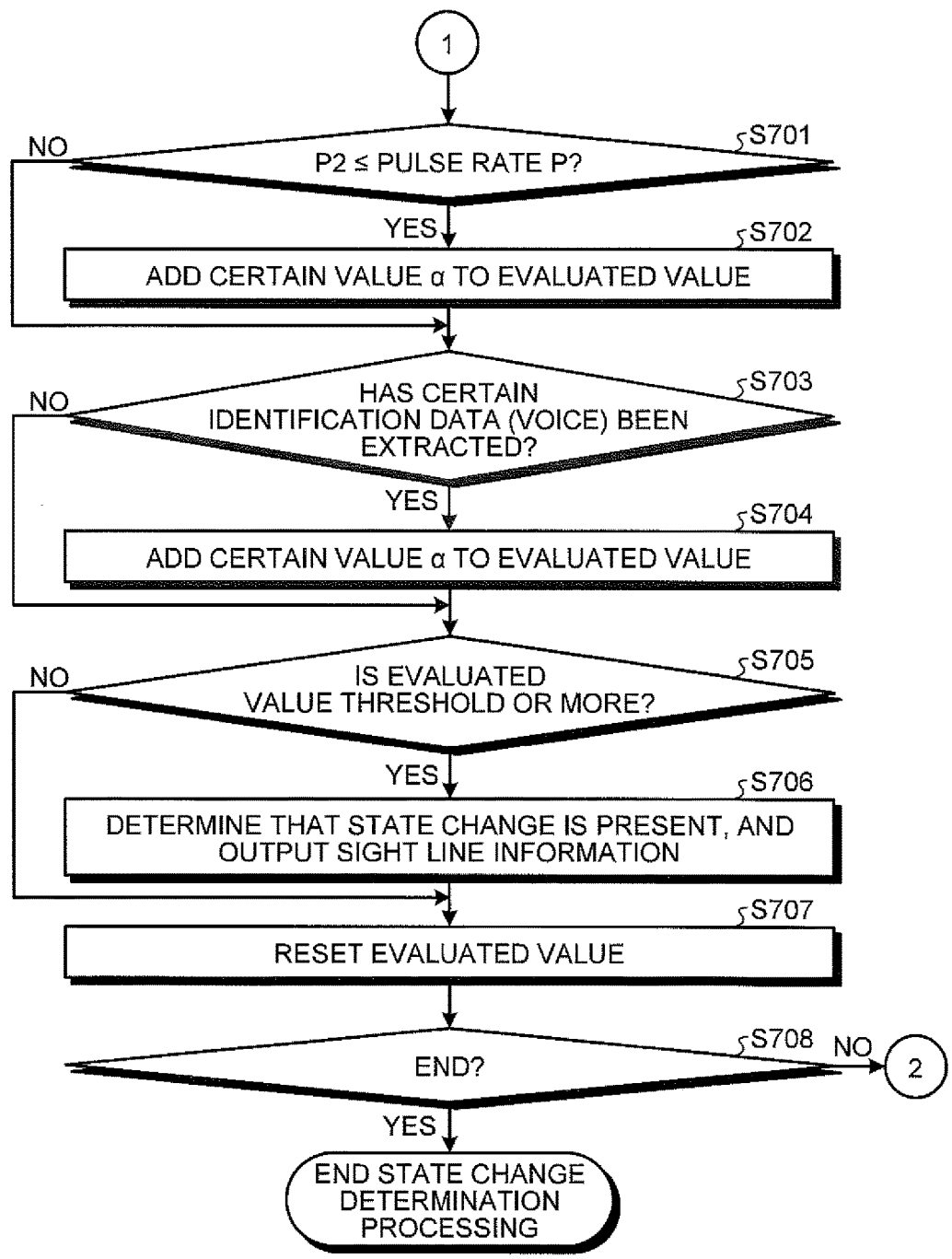

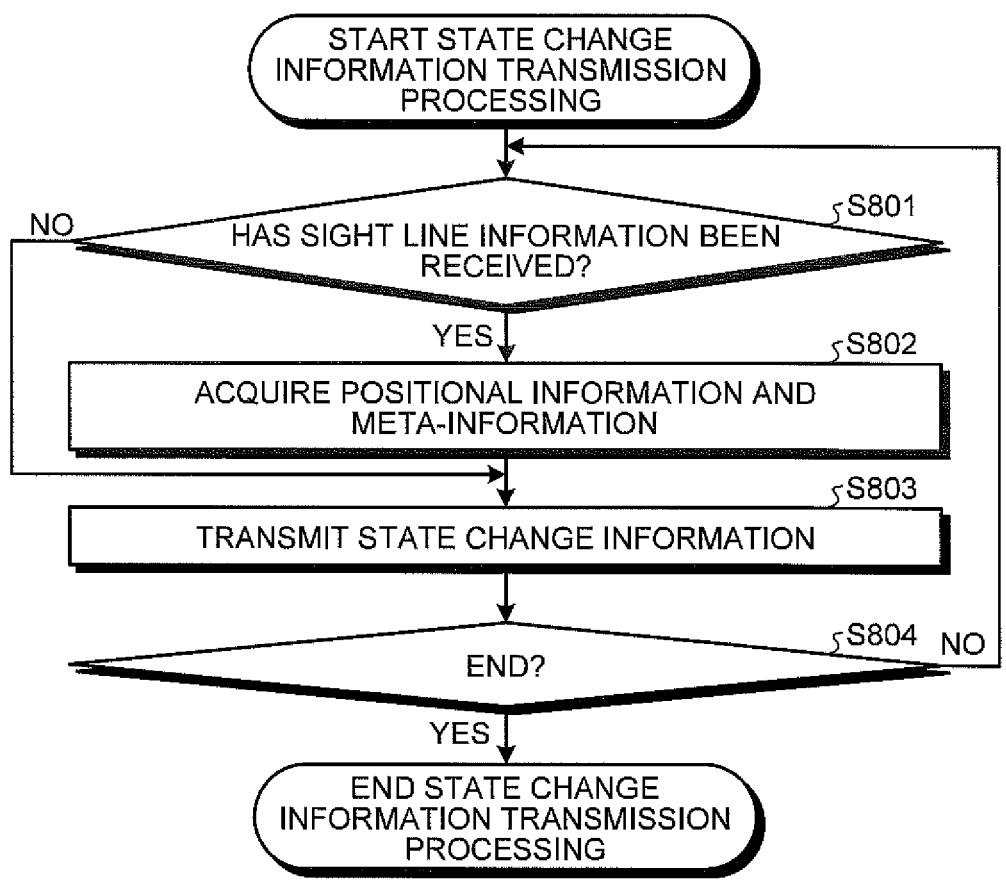

INFORMATION PROCESSING SYSTEM, MOBILE TERMINAL, SERVER APPARATUS, METHOD FOR PROCESSING INFORMATION, AND NON-TRANSITORY COMPUTER READABLE STORAGE MEDIUM

CROSS-REFERENCE TO RELATED APPLICATION(S)

The present application claims priority to and incorporates by reference the entire contents of Japanese Patent Application No. 2015-183144 filed in Japan on Sep. 16, 2015.

BACKGROUND OF THE INVENTION

1. Field of the Invention

The present invention relates to an information processing system, a mobile terminal, a server apparatus, a method for processing information, and a non-transitory computer readable storage medium.

2. Description of the Related Art

A technique has conventionally been known that collects motion information indicating motions of an indefinite number of people such as pedestrians, thereby detects the occurrence of an event (an abnormality, an intriguing event, or the like) to which a plurality of people pay attention, and estimates an area in which the event is occurring.

For example, a technique is known that collects positional information of mobile terminals carried by pedestrians or other people, thereby quickly detects a situation in which a plurality of people are stopping because of the occurrence of an abnormality, and identifies an area in which the abnormality is occurring.

Another technique is known that installs an imaging apparatus at a predetermined position, detects sight lines of a plurality of people using image information obtained by imaging an indefinite number of people such as pedestrians to identify an area on which the sight lines are focused, and thereby detects that an event has occurred in that area.

However, simply by collecting the positional information of the mobile terminals carried by pedestrians or other people as described above, it is difficult to estimate the area in which the abnormality is occurring with high precision. This is because when people are looking at an abnormality at a distance, the positional information of positions at which the people are stopping does not necessarily represent the area in which the abnormality is occurring, for example.

In contrast, the method that identifies the area on which the sight lines are focused to detect the area in which the abnormality is occurring can avoid this problem. However, there is a problem in that when sight lines of an indefinite number of people are attempted to be monitored to constantly detect an area in which an abnormality is occurring, a huge amount of data is required to be processed at high speed, causing calculation costs.

SUMMARY OF THE INVENTION

It is an object of the present invention to at least partially solve the problems in the conventional technology.

According to one aspect of an embodiment, an information processing system includes an acquiring unit that acquires motion information indicating a current motion of a user, a determining unit that compares the motion information acquired by the acquiring unit with standard information indicating a motion of the user in a predetermined state to determine presence or absence of a state change of the user, and a calculating unit that, when the determining unit determines that a state change is present, calculates an area that the user visually recognizes based on sight line information concerning a sight line of the user contained in the motion information.

The above and other objects, features, advantages and technical and industrial significance of this invention will be better understood by reading the following detailed description of presently preferred embodiments of the invention, when considered in connection with the accompanying drawings.

BRIEF DESCRIPTION OF THE DRAWINGS

FIG. 1 is a diagram of an example of an overall configuration of a sight line information collecting system;

FIG. 4 is a diagram of an example of a functional configuration of the mobile terminal;

FIG. 5 is a diagram of an example of state change determination information;

FIG. 6 is a flowchart of a procedure of state change determination processing;

FIG. 7 is a flowchart of a procedure of the state change determination processing;

FIG. 8 is a flowchart of a procedure of state change information transmission processing;

DETAILED DESCRIPTION OF THE PREFERRED EMBODIMENTS

Figure 2A:
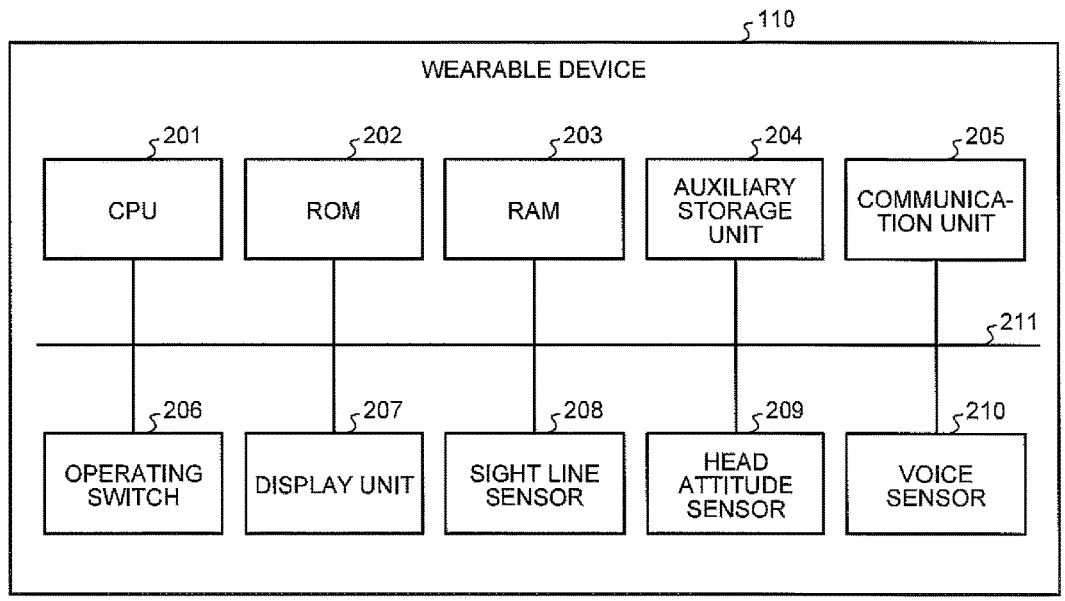
FIGS. 2A and 2B are diagrams of examples of hardware configurations of a wearable device and a mobile terminal.

The following describes embodiments with reference to the accompanying drawings. In the present specification and drawings, components having substantially the same functional configuration are denoted by the same symbols, whereby a duplicate description will be omitted.

First Embodiment

1. Overall Configuration of Sight Line Information Collecting System

First, the following describes an overall configuration of a sight line information collecting system as an example of an information processing system according to the present embodiment. FIG. 1 is a diagram of an example of the overall configuration of the sight line information collecting system.

As illustrated in FIG. 1, this sight line information collecting system 100 includes a spectacle-type wearable device 110 worn by a user 150, a mobile terminal 120 carried by the user 150, and a server apparatus 130. The wearable device 110 and the mobile terminal 120 are communicably connected with each other via short-range wireless communication. The mobile terminal 120 and the server apparatus 130 are connected with each other via a network 140 represented by the Internet, a local area network (LAN), or the like. Although the example in FIG. 1 illustrates only one user 150 wearing the wearable device 110 and carrying the mobile terminal 120, it is assumed that a plurality of users are actually present.

The wearable device 110 includes motion sensors for detecting various kinds of motions of the user 150, detects the various kinds of motions of the user 150 in real time, and transmits detected motion data (motion information indicating the motion of the user) to the mobile terminal 120. Examples of the motion sensors included in the wearable device 110 include a sight line sensor that detects the movement of an eye of the user 150 and outputs sight line data. Examples of the motion sensors included in the wearable device 110 include a head attitude sensor that detects the attitude of the head of the user 150 and outputs head attitude data and a voice sensor that detects voice uttered by the user 150 and outputs voice data.

The mobile terminal 120 receives the motion data (the sight line data, the head attitude data, and the voice data in this example) transmitted from the wearable device 110. The mobile terminal 120 includes motion sensors for detecting other motions of the user 150 that the wearable device 110 does not detect. Furthermore, the mobile terminal 120 receives motion data indicating other motions of the user 150 detected by a wearable device (not illustrated) other than the wearable device 110.

Examples of the motion sensors included in the mobile terminal 120 include a vibration sensor that detects vibrations caused by the user 150 walking or the like and outputs vibration data. Examples of the motion sensors included in the mobile terminal 120 include a global positioning system (GPS) sensor that detects the current position of the user 150 and outputs GPS data (latitude data, longitude data, and altitude data).

Examples of the motion data that the mobile terminal 120 receives from a wearable device other than the wearable device 110 include pulse wave data transmitted from a pulse wave sensor that detects a pulse wave of the user 150.

The mobile terminal 120 determines the presence or absence of a state change of the user 150 based on the motion data received from the wearable device 110 or another wearable device and the motion data that the motion sensor included in the mobile terminal 120 detects. The mobile terminal 120 generates state change information based on the sight line data acquired when it is determined that a state change is present in the user 150 and transmits the state change information to the server apparatus 130.

The mobile terminal 120 receives analysis result information from the server apparatus 130 in accordance with the transmission of the state change information and displays the analysis result information on the display unit.

The server apparatus 130 is an apparatus that analyzes the state change information transmitted from the mobile terminal 120 and transmits an analysis result to the mobile terminal 120. In the server apparatus 130, an information collection program, a state analysis program, and an analysis result transmission program are installed. The server apparatus 130 executes these computer programs and thereby functions as an information collecting unit 131, a state analyzing unit 132, and an analysis result transmitter 133.

The information collecting unit 131 receives the state change information transmitted from the mobile terminal 120. The information collecting unit 131 receives pieces of state change information transmitted from respective mobile terminals carried by the users.

The state analyzing unit 132 calculates the sight line position of the user 150 carrying the mobile terminal 120 serving as a transmission source using the state change information received by the information collecting unit 131. The state analyzing unit 132 calculates the respective sight line positions of the users, thereby identifies respective areas that a plurality of people visually recognize, calculates an area that the people visually recognize in a duplicate manner, and thereby identifies an area in which an event is occurring.

Examples of "an event is occurring" in this example include the fact that an abnormality is occurring such as a crack in the ground is occurring, a foreign object is getting caught on an electric wire, or a foreign object is lying on a road. Examples of "an event is occurring" include the fact that an event interesting people is occurring such as digital signage is being displayed or fireworks are being launched. Furthermore, the abnormality or the event interesting people are not limited to an event that is occurring while remaining at a predetermined place and may be an event accompanied by movement. Specifically, the abnormality or the event interesting people may be an event such as an advertising car has passed by or an animal that escaped has crossed.

The analysis result transmitter 133 transmits the analysis result information containing a map explicitly indicating the area in which the event is occurring identified by the state analyzing unit 132 to the mobile terminal 120 and stores the analysis result information in an analysis result storage unit 134.

2. Hardware Configurations of Respective Apparatuses

The following describes hardware configurations of respective apparatuses included in the sight line information collecting system 100.

(1) Hardware Configuration of Wearable Device

First, the following describes a hardware configuration of the wearable device 110. FIG. 2A is a diagram of an example of the hardware configuration of the wearable device 110.

As illustrated in FIG. 2A, the wearable device 110 includes a CPU 201, a read only memory (ROM) 202, a random access memory (RAM) 203, an auxiliary storage unit 204, and a communication unit 205. The wearable device 110 also includes an operating switch 206, a display unit 207, a sight line sensor 208, a head attitude sensor 209, and a voice sensor 210. The respective units of the wearable device 110 are connected with each other via a bus 211.

The CPU 201 is a computer that executes various kinds of computer programs installed in the auxiliary storage unit 204. The ROM 202 is a non-volatile memory. The ROM 202 functions as a main storage unit that stores therein various kinds of computer programs, data, and the like required for the CPU 201 to execute the various kinds of computer programs stored in the auxiliary storage unit 204. Specifically, the ROM 202 stores therein a basic input/output system (BIOS), a boot program such as an extensible firmware interface (EFI), and the like.

The RAM 203 is a volatile memory such as a dynamic random access memory (DRAM) or a static random access memory (SRAM) and functions as a main storage unit. The RAM 203 provides a work area into which the various kinds of computer programs stored in the auxiliary storage unit 204 are loaded for being executed by the CPU 201.

The auxiliary storage unit 204 stores therein various kinds of computer programs installed in the wearable device 110, data used in executing the various kinds of computer programs, and the like.

The communication unit 205 is a device for the wearable device 110 to communicate with the mobile terminal 120 via the short-range wireless communication.

The operating switch 206 is a device that enables the user 150 to input various kinds of instructions to the wearable device. The display unit 207 is a device for displaying various kinds of information to the user 150.

The sight line sensor 208 detects the movement of the eye of the user 150 and outputs sight line data. The head attitude sensor 209 detects the attitude of the head of the user 150 and outputs head attitude data. The voice sensor 210 detects the voice uttered by the user 150 and outputs voice data.

(2) Hardware Configuration of Mobile Terminal

Figure 2B:
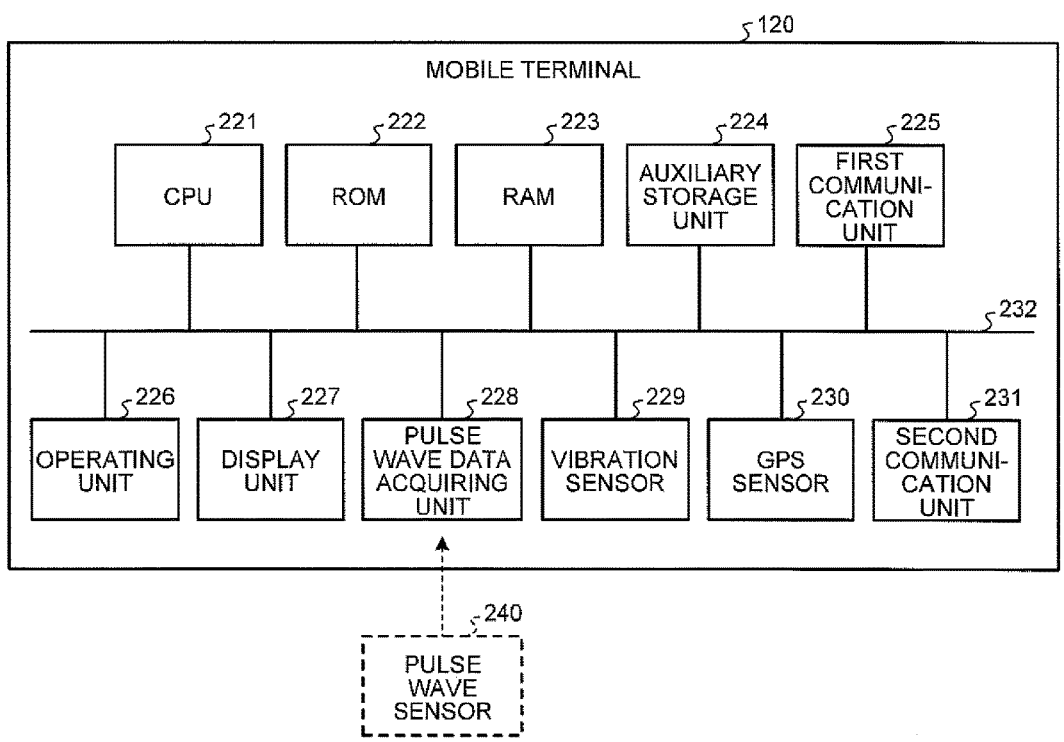

The following describes a hardware configuration of the mobile terminal 120. FIG. 2B is a diagram of an example of a hardware configuration of the mobile terminal 120.

As illustrated in FIG. 2B, the mobile terminal 120 includes a CPU 221, a ROM 222, a RAM 203, an auxiliary storage unit 204, and a first communication unit 225. The mobile terminal 120 also includes an operating unit 226, a display unit 227, a pulse wave data acquiring unit 228, a vibration sensor 229, a GPS sensor 230, and a second communication unit 231. The respective units of the mobile terminal 120 are connected with each other via a bus 232.

The CPU 221 is a computer that executes various kinds of computer programs installed in an auxiliary storage unit 224. The ROM 222 is a non-volatile memory. The ROM 222 functions as a main storage unit that stores therein various kinds of computer programs, data, and the like required for the CPU 221 to execute the various kinds of computer programs stored in the auxiliary storage unit 224. Specifically, the ROM 222 stores therein a BIOS, a boot program such as an EFI, and the like.

The RAM 223 is a volatile memory such as a DRAM or an SRAM and functions as a main storage unit. The RAM 223 provides a work area into which the various kinds of computer programs stored in the auxiliary storage unit 224 are loaded for being executed by the CPU 201.

The auxiliary storage unit 224 stores therein various kinds of computer programs installed in the mobile terminal 120, data used in executing the various kinds of computer programs, and the like.

The first communication unit 225 is a device for the mobile terminal 120 to communicate with the wearable device 110 via the short-range wireless communication.

The operating unit 226 receives input by the user 150 to the mobile terminal 120. When characters are input by the user 150, the operating unit 226 outputs text data. The display unit 227 is a device for displaying various kinds of information (the analysis result information, for example) to the user 150.

The pulse wave data acquiring unit 228, to which a pulse wave sensor 240 that a wearable device (not illustrated) includes is connected, acquires pulse wave data output in response to a pulse wave detected by the pulse wave sensor 240.

The vibration sensor 229 detects vibrations caused by the user 150 walking or the like and outputs vibration data.

The GPS sensor 230 detects the current position of the user 150 and outputs GPS data (latitude data, longitude data, and altitude data).

The second communication unit 231 is connected to the server apparatus 130 and transmits the state change information to the server apparatus 130 and receives the analysis result information from the server apparatus 130.

(3) Hardware Configuration of Server Apparatus

Figure 3:
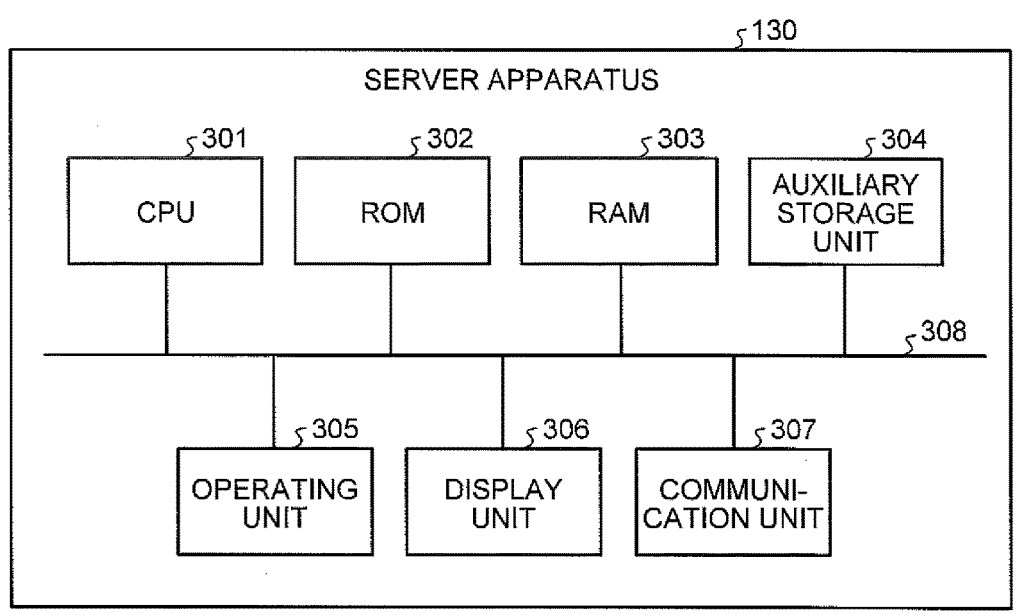
FIG. 3 is a diagram of an example of a hardware configuration of a server apparatus.

The following describes a hardware configuration of the server apparatus 130. FIG. 3 is an example of a hardware configuration of the server apparatus.

As illustrated in FIG. 3, the server apparatus 130 includes a CPU 301, a ROM 302, a RAM 303, an auxiliary storage unit 304, an operating unit 305, a display unit 306, and a communication unit 307. The respective units of the server apparatus 130 are connected with each other via a bus 308.

The CPU 301 is a computer that executes various kinds of computer programs (information collection program, state analysis program, and analysis result transmission program) installed in the auxiliary storage unit 304. The ROM 302 is a non-volatile memory. The ROM 302 functions as a main storage unit that stores therein various kinds of computer programs, data, and the like required for the CPU 301 to execute the various kinds of computer programs stored in the auxiliary storage unit 304. Specifically, the ROM 302 stores therein a BIOS, a boot program such as an EFI, and the like.

The RAM 303 is a volatile memory such as a DRAM or an SRAM and functions as a main storage unit. The RAM 303 provides a work area into which the various kinds of computer programs stored in the auxiliary storage unit 304 are loaded for being executed by the CPU 201.

The auxiliary storage unit 304 stores therein various kinds of computer programs installed in the server apparatus 130, data used in executing the various kinds of computer programs, and the like.

The operating unit 305 is a device that receives input by an administrator of the server apparatus 130 to the server apparatus 130. The display unit 306 is a device that displays internal information of the server apparatus 130. The communication unit 307 is a device for performing communication with the mobile terminal 120.

3. Functional Configuration of Mobile Terminal

The following describes a functional configuration of the mobile terminal 120. FIG. 4 is a diagram of an example of a functional configuration of the mobile terminal. As illustrated in FIG. 4, the mobile terminal 120 includes a sight line data analyzing unit 401, a head attitude data analyzing unit 402, a voice data analyzing unit 403, a vibration data analyzing unit 404, a pulse wave data analyzing unit 405, a text data analyzing unit 406, and a GPS data analyzing unit 407. The mobile terminal 120 also includes a state change determining unit 410 and a state change information transmitter 420.

The sight line data analyzing unit 401 analyzes the sight line data received from the wearable device 110, thereby calculates a focal length and a sight line direction of the eye of the user 150, and notifies the state change determining unit 410 of focal length data and sight line direction data.

The head attitude data analyzing unit 402 analyzes the head attitude data received from the wearable device 110, thereby calculates up-and-down and side-to-side shaking angles of the user 150, and notifies the state change determining unit 410 of up-and-down shaking angle data and side-to-side shaking angle data.

The voice data analyzing unit 403 analyzes the voice data received from the wearable device 110, thereby identifies voice uttered by the user 150, and notifies the state change determining unit 410 of identification data (voice).

The vibration data analyzing unit 404 analyzes the vibration data received from the wearable device 110, thereby calculates a travel speed when the user 150 walks or the like, and notifies the state change determining unit 410 of travel speed data.

The pulse wave data analyzing unit 405 analyzes the pulse wave data acquired by the pulse wave data acquiring unit 228, thereby calculates a pulse rate per unit time, and notifies the state change determining unit 410 of pulse rate data.

The text data analyzing unit 406 analyzes the text data output from the operating unit 226 and notifies the state change determining unit 410 of the text data. Examples of the text data output from the operating unit 226 include text data obtained by identifying character input to Twitter and text data obtained by identifying characters input as a search query.

The GPS data analyzing unit 407 transmits the GPS data (the latitude data, the longitude data, and the altitude data) that the GPS sensor 230 has acquired to the state change information transmitter 420.

The state change determining unit 410 refers to a state change determination information DB 430 that stores therein standard information indicating motions of the user in a predetermined state (a stationary state) and compares data (determination data) corresponding to the motion data indicating the current motion of the user 150 with the standard information. The state change determining unit 410 determines the presence or absence of a state change of the user 150 based on a result of the comparison between the standard information and the determination data. The stationary state refers to a state of the user 150 when no event is occurring, and the standard information indicating the motion of the user in the stationary state is determined based on the determination data corresponding to past motion data acquired in the stationary state. A method of determination is not limited; a value deviated from the determination data in the stationary state by x % may be determined to be the standard information, for example. The past motion data for use in the determination may be past motion data of another user, not limited to the past motion data of the user. The determination of the standard information may be performed by the user of the mobile terminal 120 or performed by the administrator of the server apparatus 130. Furthermore, the determined standard information may be configured to be able to be finely adjusted later, and the fine adjustment in that case may be performed by the user of the mobile terminal 120 or performed by the administrator of the server apparatus 130.

Specifically, the standard information is determined based on a focal length calculated using past sight line data acquired in the stationary state. Alternatively, the standard information is determined based on a pulse rate calculated using past pulse wave data acquired in the stationary state.

When determining that the state of the user 150 has changed based on the determination data corresponding to the current motion data of the user 150, the state change determining unit 410 transmits sight line information to the state change information transmitter 420. Specifically, the state change determining unit 410 notifies the state change information transmitter 420 of the focal length data and the sight line direction data acquired when determining that the state of the user 150 has changed as the sight line information.

Upon reception of the sight line information from the state change determining unit 410, the state change information transmitter 420 generates the state change information containing the GPS data notified of from the GPS data analyzing unit 407 at the reception and the text data notified of from the text data analyzing unit 406 around the reception. The state change information transmitter 420 transmits the generated state change information to the server apparatus 130. Furthermore, the state change information transmitter 420 stores history information indicating the fact that the state change information has been transmitted to the server apparatus 130 in a history information DB 440.

The mobile terminal 120 thus transmits the state change information to the server apparatus 130 when the state change determining unit 410 determines that the state of the user 150 has changed. Consequently, a data amount to be analyzed by the server apparatus 130 can be reduced remarkably compared with a method that transmits the sight line information in its entirety. Consequently, calculation costs in the server apparatus 130 can be reduced.

In other words, when mobile terminals 120 of the present embodiment are carried by a plurality of people, a system that identifies an area in which an event to which a plurality of people pay attention is occurring based on the sight lines of the people can be achieved at low cost.

4. Description of State Change Determination Information

The following describes state change determination information stored in the state change determination information DB 430. FIG. 5 is a diagram of an example of the state change determination information. As illustrated in FIG. 5, this state change determination information 500 contains "determination data" and "standard information for determining that state of user is not stationary state" as information items.

The "determination data" stores therein pieces of data to be compared with the standard information for determining that the state of user is not stationary state, or the data (determination data) corresponding to the motion data. The example in FIG. 5 stores therein focal length data L, time T during which sight line direction is constant, side-to-side shaking angle $\theta$, up-and-down shaking angle $\varphi$, travel speed V, identification data (voice), and pulse rate P as the "determination data."

The "standard information for determining that state of user is not stationary state" stores therein thresholds for determining that the state of the user 150 is not the stationary state concerning respective kinds of pieces of determination data stored in the "determination data." The example in FIG. 5 illustrates that it is determined that the user 150 has become not to be the stationary state when the focal length data L is L1 or more. Similarly, the example in FIG. 5 illustrates that it is determined that the user 150 has become not to be the stationary state when the time T during which the sight line direction is constant is T1 or more. The example in FIG. 5 illustrates that it is determined that the user 150 has become not to be the stationary state when the side-to-side shaking angle $\theta$ is $(-\theta 1)$ or less or $(+\theta 1)$ or more or when the up-and-down shaking angle $\varphi$ is $(-\varphi 1)$ or less or $(+\varphi 1)$ or more. The example in FIG. 5 illustrates that it is determined that the user 150 has become not to be the stationary state when the travel speed V is zero, when predetermined identification data (voice) is extracted, or when the pulse rate P is P2 or more.

5. Procedure of State Change Determination Processing

The following describes a procedure of the state change determination processing by the state change determining unit 410. FIG. 6 and FIG. 7 are flowcharts of a procedure of the state change determination processing.

At Step S601, the state change determining unit 410 substitutes an initial value (=0) for an evaluated value for determining the presence or absence of a state change.

At Step S602, the state change determining unit 410 determines whether the focal length data L is L1 or more. If it is determined that the focal length data L is L1 or more at Step S602, the state change determining unit 410 determines that the user 150 has become not to be the stationary state and adds a predetermined value α to the evaluated value at Step S603. In contrast, if it is determined that the focal length data L is not L1 or more at Step S602, the process advances to Step S604.

At Step S604, the state change determining unit 410 determines whether the time T during which the sight line direction is constant is T1 or more. If it is determined that the time T is T1 or more at Step S604, the state change determining unit 410 determines that the user 150 has become not to be the stationary state and adds the predetermined value α to the evaluated value at Step S605. In contrast, if it is determined that the time T is not T1 or more at Step S604, the process advances to Step S606.

At Step S606, the state change determining unit 410 determines whether the side-to-side shaking angle θ is (−θ1) or less or (+θ1) or more. The state change determining unit 410 determines whether the up-and-down shaking angle φ is (−φ1) or less or (+φ1) or more.

If it is determined that any of the conditions is satisfied at Step S606, the state change determining unit 410 determines that the user 150 has become not to be the stationary state and adds the predetermined value α to the evaluated value at Step S607. In contrast, if it is determined that none of the conditions is satisfied at Step S606, the process advances to Step S608.

At Step S608, the state change determining unit 410 determines whether the travel speed V is zero. If it is determined that the travel speed V is zero at Step S608, the state change determining unit 410 determines that the user 150 has become not to be the stationary state and adds the predetermined value α to the evaluated value at Step S609. In contrast, if it is determined that the travel speed V is not zero at Step S608, the process advances to Step S701 in FIG. 7

At Step S701, the state change determining unit 410 determines whether the pulse rate P is P1 or more. If it is determined that the pulse rate P is P1 or more at Step S610, the state change determining unit 410 determines that the user 150 has become not to be the stationary state and adds the predetermined value α to the evaluated value at Step S702. In contrast, if it is determined that the pulse rate P is not P1 or more at Step S701, the process advances to Step S703.

At Step S703, the state change determining unit 410 determines whether the predetermined identification data (voice) has been extracted. If it is determined the predetermined identification data (voice) has been extracted at Step S703, the state change determining unit 410 determines that the user 150 has become not to be the stationary state and adds the predetermined value α to the evaluated value at Step S704. In contrast, if it is determined the predetermined identification data (voice) has not been extracted at Step S703, the process advances to Step S705.

At Step S705, the state change determining unit 410 determines whether the evaluated value is a predetermined threshold or more. If it is determined that the evaluated value is the predetermined threshold or more at Step S705, the process advances to Step S706. At Step S706, the state change determining unit 410 determines that the state of the user 150 has changed and notifies the state change information transmitter 420 of the focal length data and the sight line direction data acquired in this step as the sight line information.

In contrast, if it is determined that the evaluated value is not the predetermined threshold or more at Step S705, the process advances to Step S707. At Step S707, the state change determining unit 410 resets the evaluated value.

At Step S708, the state change determining unit 410 determines whether the state change determination processing is to be ended, and if it is determined that the state change determination processing is not to be ended, the process returns to Step S602. Consequently, determination on whether the state of the user 150 has changed can be performed at every predetermined control period.

In contrast, if it is determined that the state change determination processing is to be ended at Step S708, the state change determination processing is ended.

6. Procedure of State Change Information Transmission Processing

The following describes a procedure of state change information transmission processing by the state change information transmitter 420. FIG. 8 is a flowchart of a procedure of the state change information transmission processing.

At Step S801, the state change information transmitter 420 determines whether the sight line information has been received from the state change determining unit 410. If it is determined that the sight line information has not been received at Step S801, the process advances to Step S804.

In contrast, if it is determined that the sight line information has been received at Step S801, the process advances to Step S802. At Step S802, the state change information transmitter 420 acquires the text data from the text data analyzing unit 406. The text data acquired from the text data analyzing unit 406 is used as meta-information for identifying an event that has occurred. The state change information transmitter 420 acquires the GPS data (the latitude data, the longitude data, and the altitude data) from the GPS data analyzing unit 407. The GPS data acquired from the GPS data analyzing unit 407 is used as positional information for identifying the current position of the user 150.

At Step S803, the state change information transmitter 420 transmits the acquired sight line information, positional information, and meta-information to the server apparatus 130 as the state change information.

At Step S804, the state change information transmitter 420 determines whether the state change information transmission processing is to be ended, and if it is determined that the state change information transmission processing is not to be ended, the process returns to Step S801. In contrast, if it is determined that the state change information transmission processing is to be ended, the state change information transmission processing is ended.

7. Functional Configuration of Server Apparatus

Figure 9:
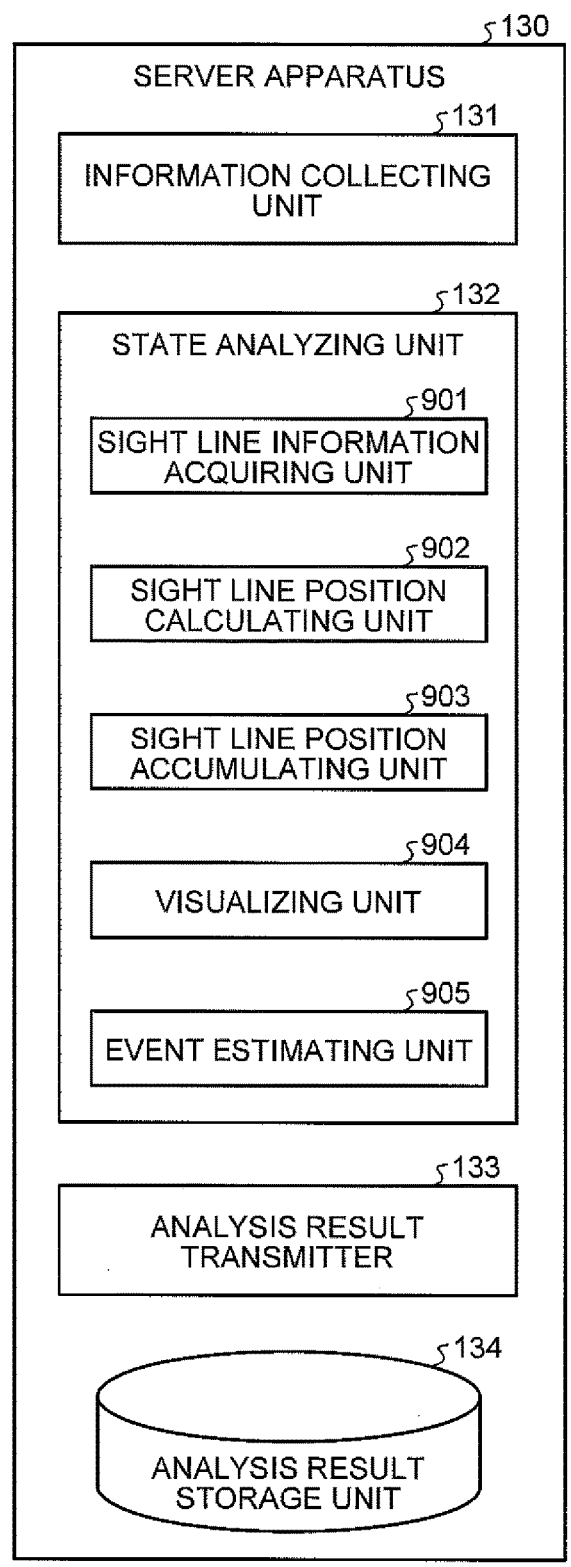
FIG. 9 is a diagram of an example of a functional configuration of the server apparatus.

The following describes a functional configuration of the server apparatus 130. FIG. 9 is a diagram of an example of the functional configuration of the server apparatus. As described above, the server apparatus 130 includes the information collecting unit 131, the state analyzing unit 132, and the analysis result transmitter 133. The details of the information collecting unit 131 and the analysis result transmitter 133 have already been described, and the following describes details of the state analyzing unit 132.

The state analyzing unit 132 includes a sight line information acquiring unit 901, a sight line position calculating unit 902, a sight line position accumulating unit 903, a visualizing unit 904, and an event estimating unit 905.

The sight line information acquiring unit 901 acquires the sight line information, the positional information, and the meta-information contained in the state change information collected by the information collecting unit 131.

The sight line position calculating unit 902 calculates the sight line position of the user 150 based on the sight line information and the positional information acquired by the sight line information acquiring unit 901.

Specifically, the sight line position calculating unit 902 generates a vector with the latitude data, the longitude data, and the altitude data contained in the positional information as an initial point in predetermined three-dimensional coordinate axes. In this process, the length of the vector is determined based on the focal length data contained in the sight line information, and the direction of the vector is determined based on the sight line direction data contained in the sight line information.

The sight line position calculating unit 902 calculates an area with a size determined in advance containing a final point of the generated vector (a visually recognizable area when the final point of the generated vector is designated as the sight line position) as an area that the user 150 visually recognizes. The sight line position calculating unit 902 performs weighting for the area that the user 150 visually recognizes with the final point of the vector as a maximum value and with a peripheral part of the area as a minimum value.

When an area that a plurality of users visually recognize has been calculated by the sight line position calculating unit 902, the sight line position accumulating unit 903 calculates an area that the users visually recognize in a superimposed manner to identify an area in which an event has occurred. Specifically, the sight line position accumulating unit 903 adds respective weighted values within the area that the users visually recognize for respective coordinate positions. An area containing a coordinate position having a weighted value of a predetermined threshold or more (that is, the area that the users visually recognize in a superimposed manner) among the weight values of the respective coordinate positions is identified as the area in which the event has occurred.

The visualizing unit 904 generates a map explicitly indicating the area in which the event has occurred and notifies the analysis result transmitter 133 of the map.

The event estimating unit 905 analyzes the meta-information acquired by the sight line information acquiring unit 901 to estimate the event that has occurred. When a state change of the user 150 is present, there is a high probability that contents tweeted in Twitter or a search query used by the user 150 is information related to the event that has occurred, for example. The meta-information acquired by the sight line information acquiring unit 901 contains these pieces of information input by the user 150 around the presence of the state change of the user 150, whereby the event estimating unit 905 analyzes the meta-information and can thereby estimate the event that has occurred.

The event estimating unit 905 may estimate the event that has occurred using information other than the meta-information contained in the state change information. The event that has occurred may be estimated using contents tweeted in Twitter by a user other than the user 150 or a search query used by a user other than the user 150 in a time zone during which the state change information was acquired, for example. The contents tweeted in Twitter by a user other than the user 150 or the search query used by a user other than the user 150 may be acquired by the server apparatus 130 from another server apparatus (not illustrated) or the like, for example.

The event estimating unit 905 notifies the analysis result transmitter 133 of an estimation result about the event that has occurred.

Consequently, the analysis result transmitter 133 can transmit the analysis result information containing the map explicitly indicating the area in which the event has occurred and the estimation result about the event that has occurred to the mobile terminal 120. The analysis result transmitter 133 stores the analysis result information transmitted to the mobile terminal 120 in the analysis result storage unit 134.

8. Description of Processing to Identify Area in which Event is Occurring

Figure 10A:
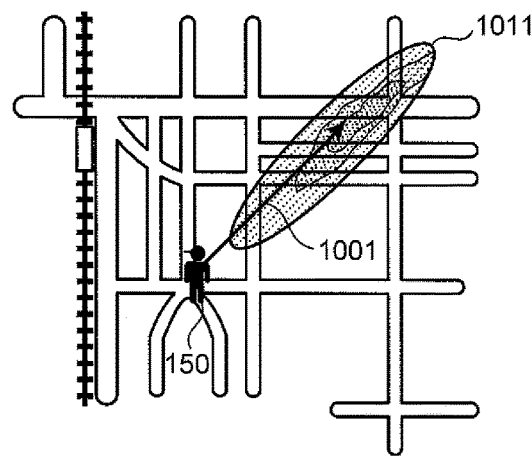
FIGS. 10A to 10C are diagrams for illustrating processing until an area in which an event is occurring is identified.
Figure 10B:
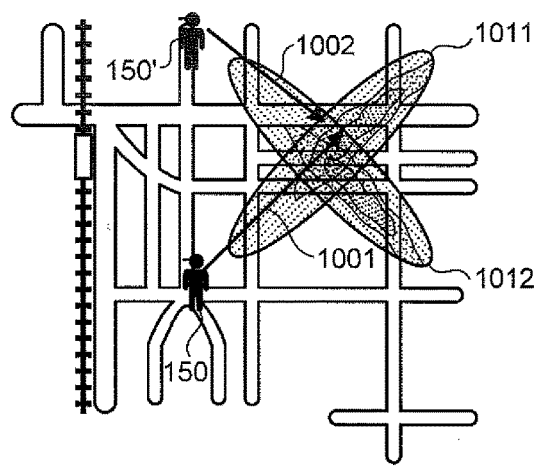
Figure 10C:
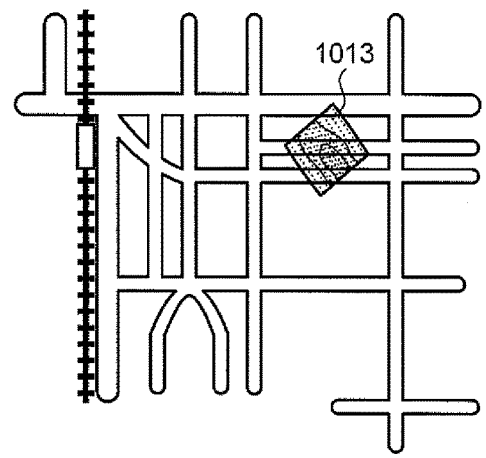

The following describes a procedure of processing until the state analyzing unit 132 identifies an area in which an event is occurring with reference to FIGS. 10A to 10C. FIGS. 10A to 10C are diagrams for illustrating processing until an area in which an event is occurring is identified based on the sight line position of a user. FIGS. 10A to 10C are illustrated by two-dimensional coordinate axes for simplifying the description.

FIG. 10A is a diagram illustrating an area that the user 150 visually recognizes calculated by the sight line position calculating unit 902. In FIG. 10A, a vector 1001 indicates a vector with the current position identified by the positional information of the user 150 as an initial point and with the sight line position identified by the sight line information of the user 150 as a final point. An area 1011 is an area with a size determined in advance containing the final point of the vector 1001. Color density within the area 1011 indicates weighted values within the area.

Similarly, FIG. 10B is a diagram of an area that a user 150' visually recognizes calculated by the sight line position calculating unit 902. In FIG. 10B, a vector 1002 indicates a vector with the current position identified by the positional information of the user 150' as an initial point and with the sight line position identified by the sight line information of the user 150' as a final point. An area 1012 is an area with a size determined in advance containing the final point of the vector 1002. Color density within the area 1012 indicates weighted values within the area.

FIG. 10C illustrates a situation in which the sight line position accumulating unit 903 adds the weighted values within the respective areas that the user 150 and the user 150' visually recognize calculated by the sight line position calculating unit 902 and extracts a coordinate position having a weighted value of the predetermined threshold or more.

In FIG. 10C, an area 1013 is an area identified as an area in which an event has occurred by the sight line position accumulating unit 903. An area in which an event has occurred is thus identified based on pieces of sight line information of a plurality of users, whereby reliability of the area in which the event has occurred can be increased compared with a case in which the area in which the event has occurred is identified based on the sight line information of one user.

As is clear from the foregoing description, the sight line information collecting system, which is an example of the information processing system according to the present embodiment, is:

- configured to determine the presence or absence of the state change of the user based on the motion data indicating the motion of the user carrying the mobile terminal;
- configured to transmit the sight line information and the positional information acquired when it is determined that the state change of the user is present to the server apparatus; and
- configured to calculate the area that the user visually recognizes based on the sight line information and the positional information transmitted from the mobile terminal and to identify the area that a plurality of users visually recognize in a superimposed manner as the area in which the event has occurred.

Consequently, the sight line information collecting system, which is an example of the information processing system according to the present embodiment, can reduce the amount of data of the sight line information and the positional information analyzed by the server apparatus in identifying the area in which the event has occurred. In other words, a system that identifies an area in which an event to which a plurality of people pay attention is occurring based on the sight lines of the people can be achieved at low cost.

Second Embodiment

In the first embodiment, in the state change determination processing, when it is determined that the user 150 has become not to be the stationary state based on the respective pieces of determination data, the state change determining unit 410 continues to add the same value to the evaluated value. In contrast, in a second embodiment, different values are added to the evaluated value in accordance with the type of the determination data. This is because in identifying the presence or absence of the state change of the user 150, the correlation between the determination data and the presence or absence of the state change of the user 150 varies depending on the type of the determination data. The following describes the second embodiment focusing on differences from the first embodiment.

Figure 11:
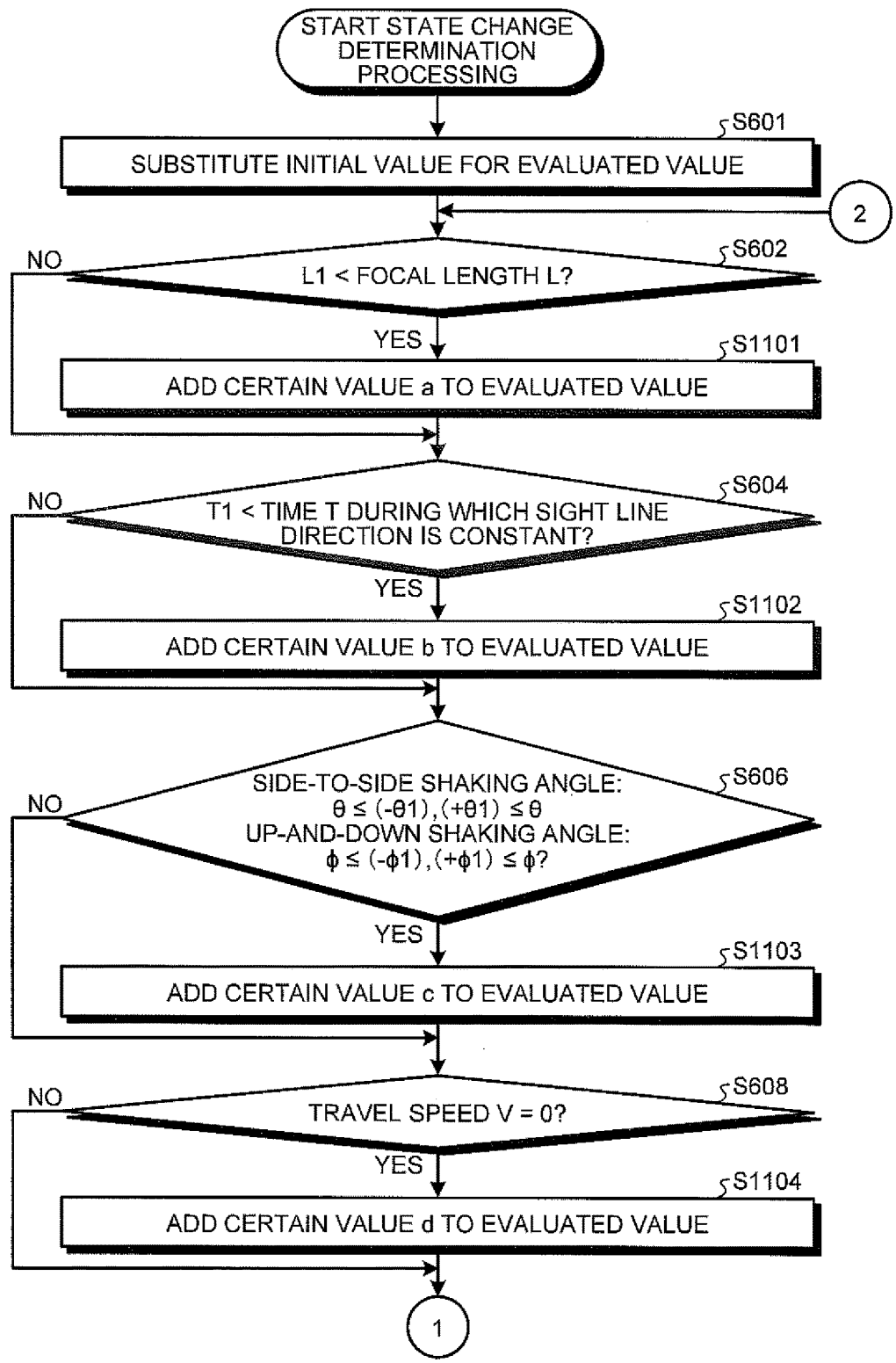
FIG. 11 is a flowchart of a procedure of the state change determination processing.
Figure 12:
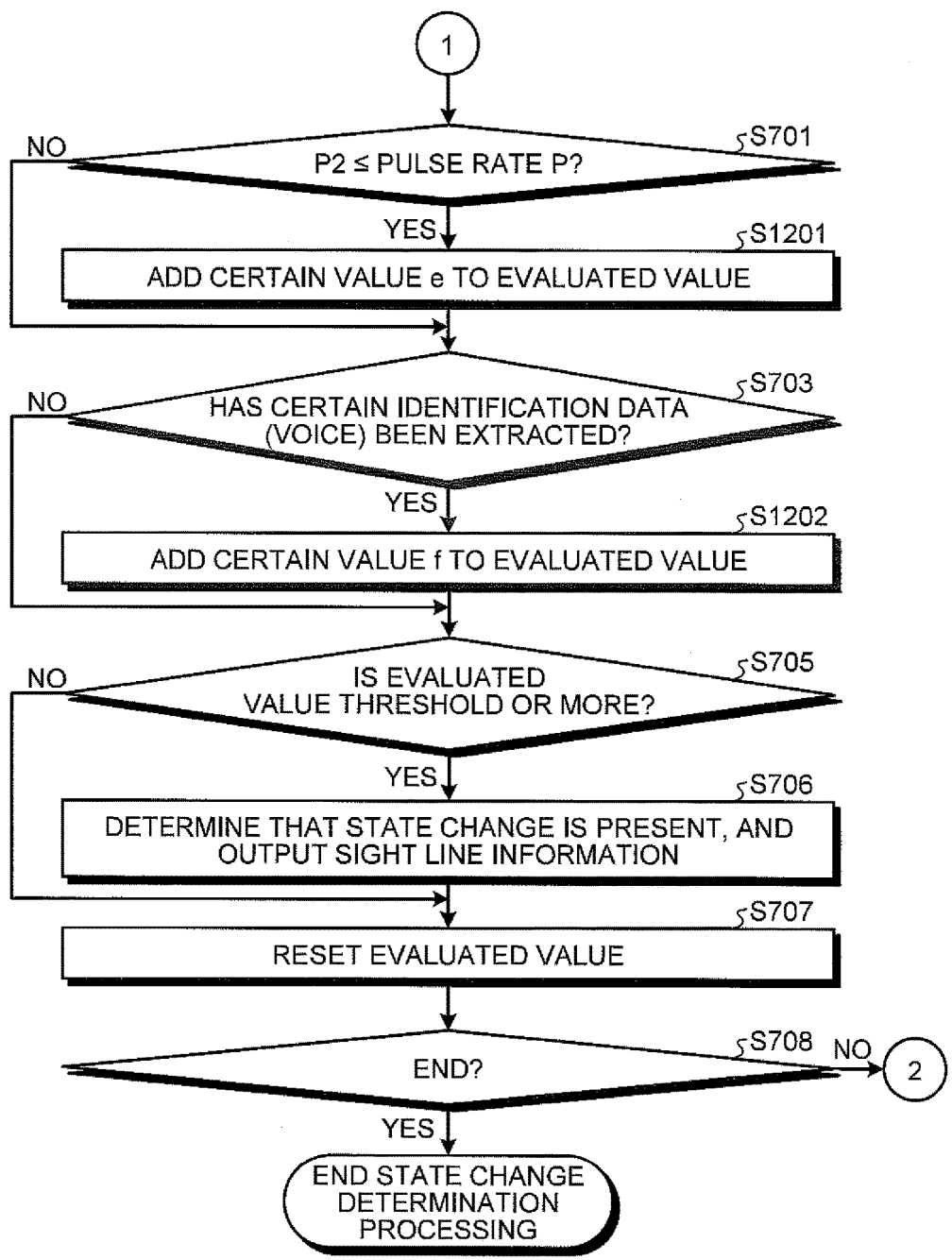
FIG. 12 is a flowchart of a procedure of the state change determination processing.

FIG. 11 and FIG. 12 are flowcharts of a procedure of the state change determination processing. Differences from the flowcharts of the state change determination processing illustrated in FIG. 6 and FIG. 7 are in Steps S1101, S1102, S1103, S1104, S1201, and S1202.

At Step S1101, the state change determining unit 410 adds a predetermined value a to the evaluated value. At Step S1102, the state change determining unit 410 adds a predetermined value b to the evaluated value. Similarly, at Steps S1103, S1104, S1201, and S1202, the state change determining unit 410 adds predetermined values c, d, e, and f, respectively, to the evaluated value.

The predetermined values a to f are values different from each other and are determined based on results of past state change determination processing, for example. The different predetermined values are thus added to the evaluated value in accordance with the fact that any determination data has exceeded the standard information, whereby the evaluated value corresponding to the correlation between the type of the determination data and the presence or absence of the state change of the user 150 can be calculated.

Consequently, the present embodiment can determine the presence or absence of the state change of the user 150 with high precision.

Third Embodiment

In the first embodiment, one piece of state change determination information 500 is prepared in advance for each user, and the state change determining unit 410 refers to the state change determination information 500, whereby the presence or absence of the state change of the user is determined. However, the standard information for use in the determination on whether the state of the user has changed varies depending on a situation in which the user is present.

Given this situation, a third embodiment takes past behavior patterns of the user into consideration, prepares a plurality of pieces of state change determination information in advance, and refers to the state change determination information corresponding to the current situation in which the user is present, thereby determining the presence or absence of the state change of the user. The following describes the third embodiment focusing on differences from the first embodiment.

1. Functional Configuration of Mobile Terminal

Figure 13:
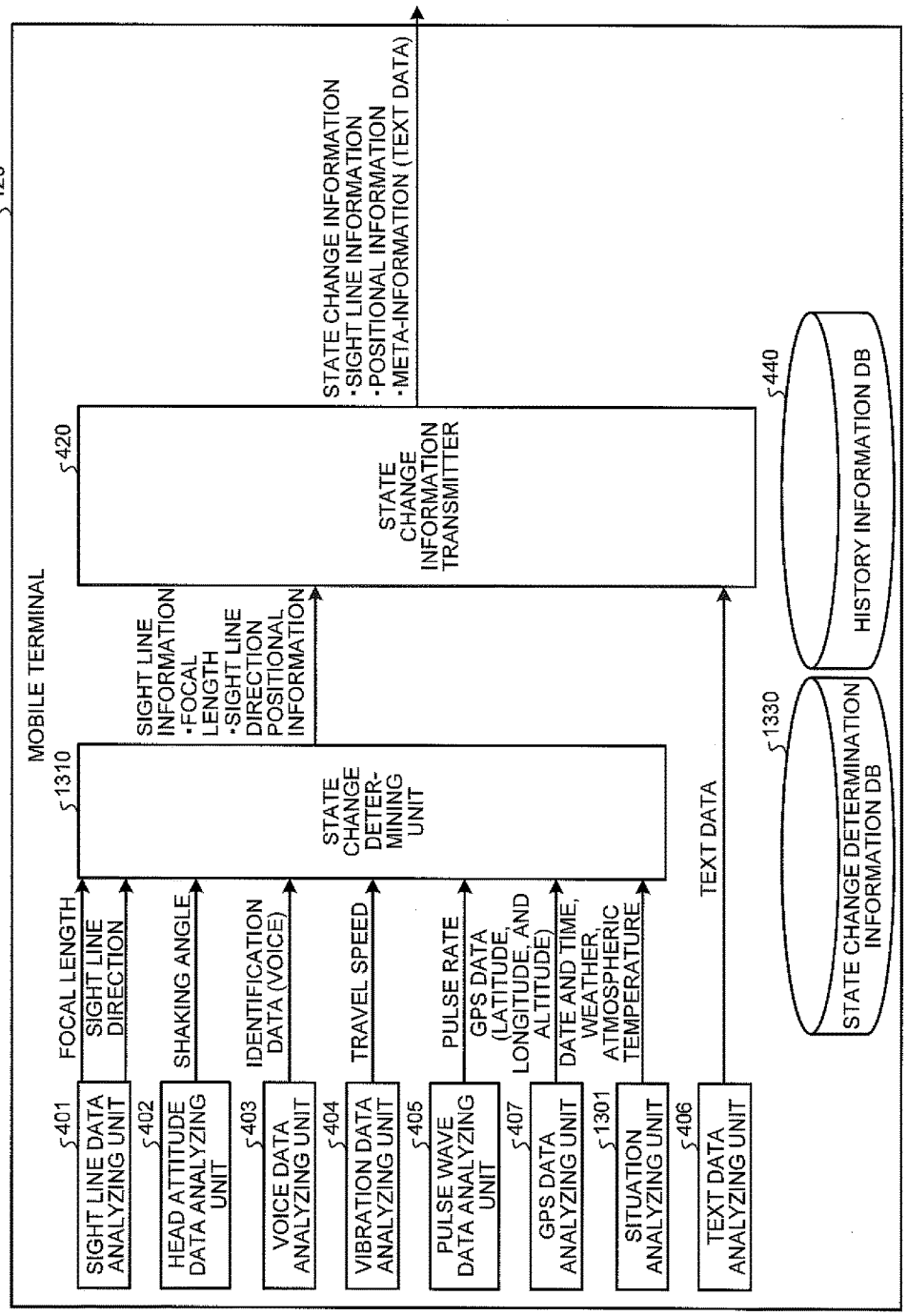
FIG. 13 is a diagram of an example of the functional configuration of the mobile terminal.

First, the following describes a functional configuration of the mobile terminal 120. FIG. 13 is a diagram of an example of the functional configuration of the mobile terminal. One difference from FIG. 4 is the fact that a situation analyzing unit 1301 is added. Another difference from FIG. 4 is the fact that a function of a state change determining unit 1310 is different from the function of the state change determining unit 410 in FIG. 4. Further another difference from FIG. 4 is the fact that information stored in a state change determination information DB 1330 is different from the information stored in the state change determination information DB 430 in FIG. 4.

The situation analyzing unit 1301 acquires a parameter indicating a situation in which the user 150 is present and notifies the state change determining unit 1310 of the parameter. In the present embodiment, the parameter indicating the situation in which the user 150 is present contains information indicating date and time, weather, and atmospheric temperature; not limited to date and time, weather, and atmospheric temperature, information other than those may be contained so long as the information has influence on the behavior pattern of the user 150.

The state change determining unit 1310 refers to the state change determination information DB 1330 that stores therein the standard information indicating the motion of the user in the predetermined state (the stationary state) and compares the standard information and the data (the determination data) corresponding to the motion data indicating the current motion of the user 150. In this process, the state change determining unit 1310 reads the standard information corresponding to the parameter indicating the situation in which the user 150 is currently present, notified of from the situation analyzing unit 1301, from the state change determination information DB 1330.

It is assumed that the state change determination information DB 1330 stores therein the state change information in which pieces of standard information that vary depending on the situation in which the user 150 is present are defined.

Figure 14:
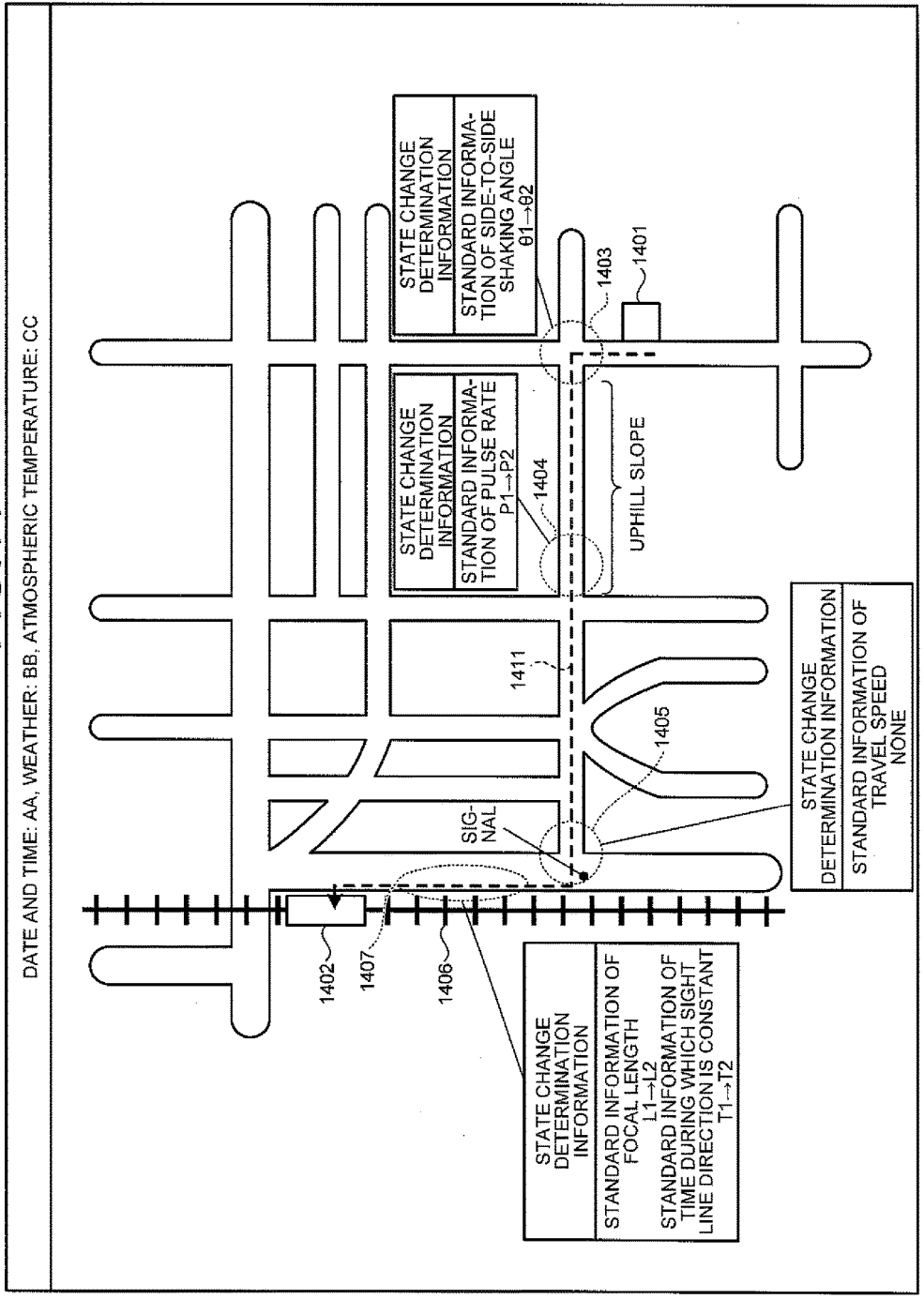
FIG. 14 is a diagram for illustrating the state change determination information in which pieces of standard information are defined under respective situations.
Figure 15:
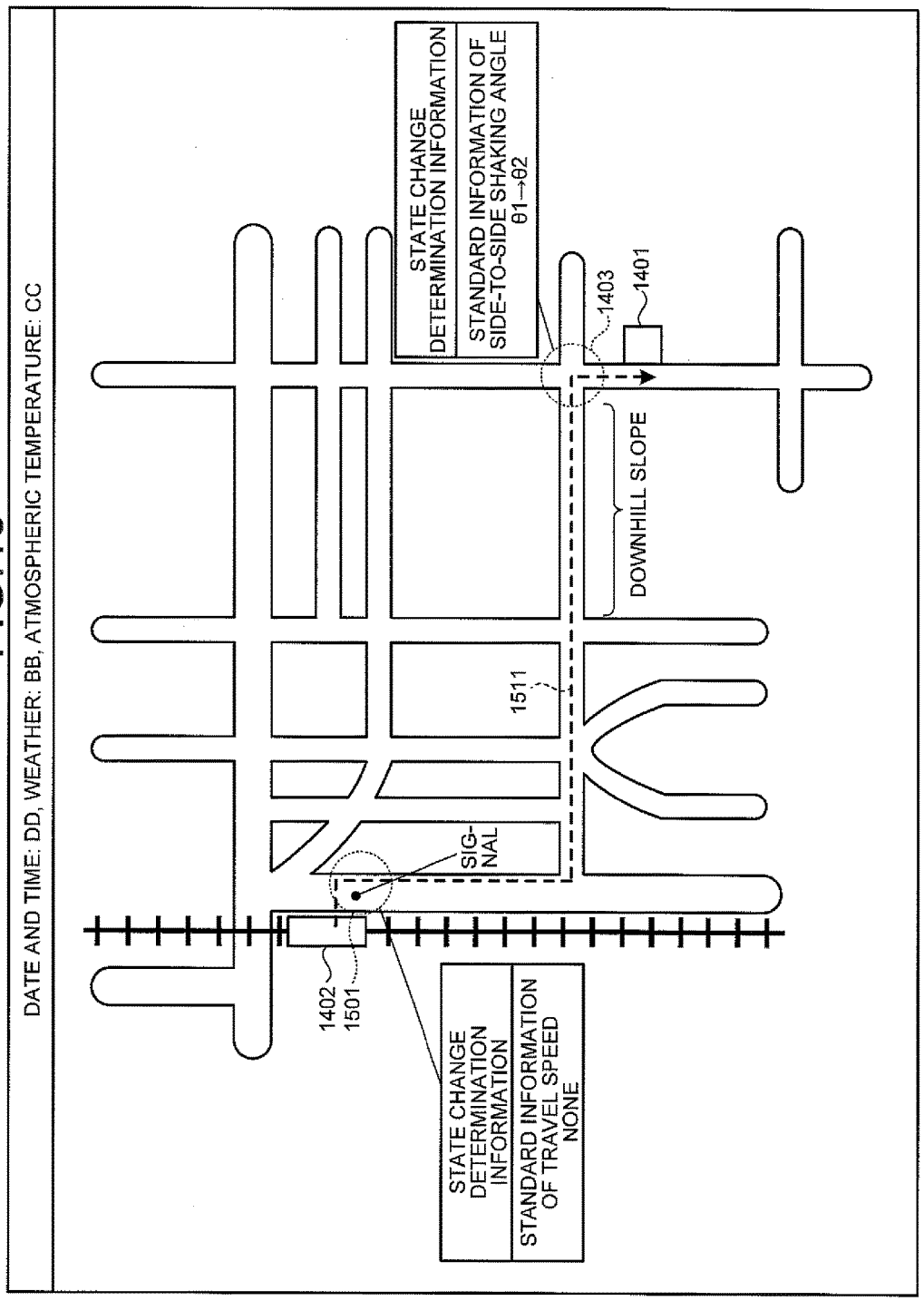
FIG. 15 is a diagram for illustrating the state change determination information in which pieces of standard information are defined under respective situations.
Figure 16:
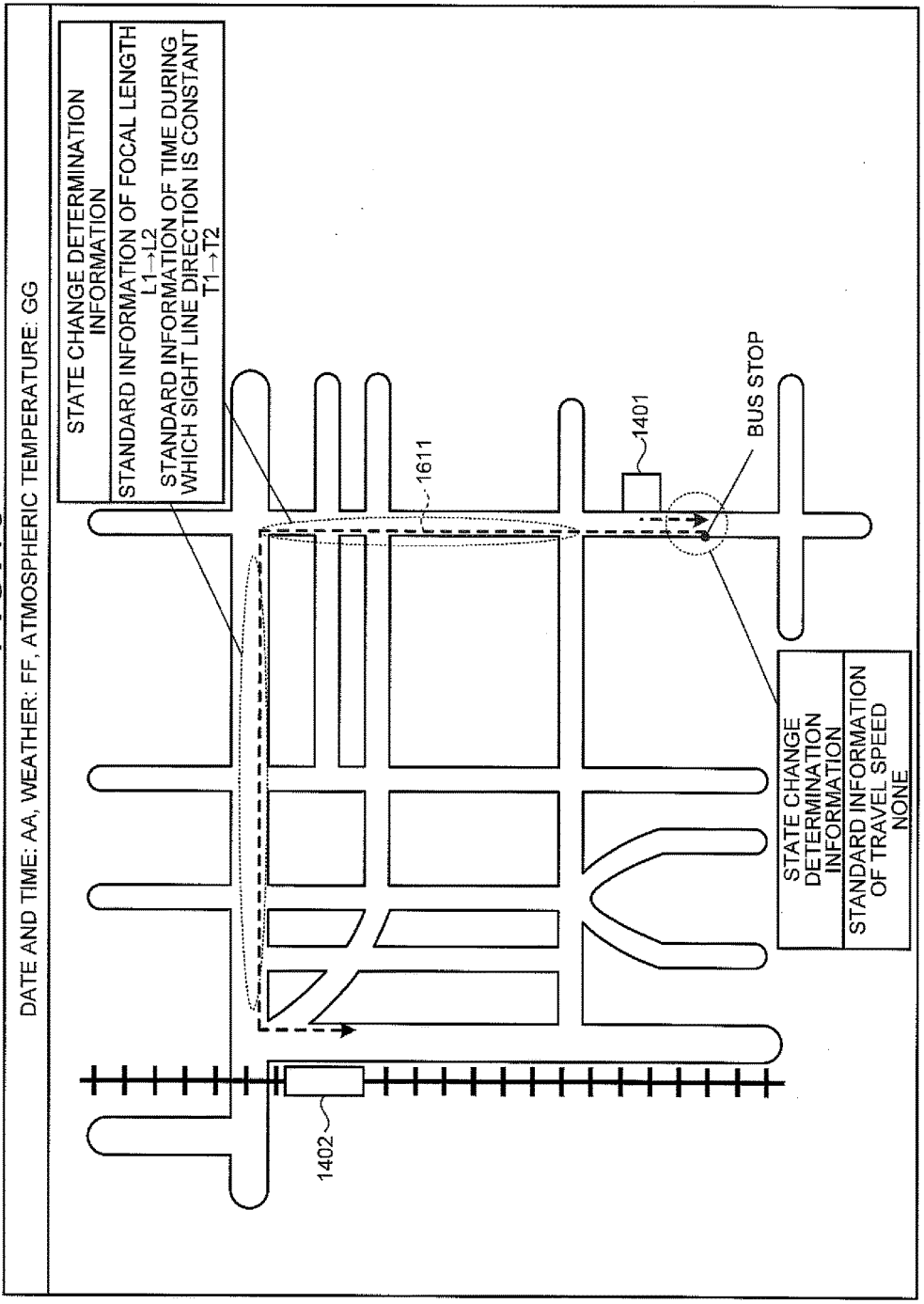
FIG. 16 is a diagram for illustrating the state change determination information in which pieces of standard information are defined under respective situations.

FIG. 14 to FIG. 16 are diagrams for illustrating the state change determination information in which pieces of standard information are defined under respective situations.

The examples in FIG. 14 to FIG. 16 illustrate that different pieces of state change determination information are prepared in accordance with various situations such as date and time, weather, or atmospheric temperature.

FIG. 14 is a diagram for illustrating the state change determination information when date and time="AA," weather="BB," and atmospheric temperature="CC." When it is assumed that date and time="AA" is what is called a commuting time zone, and when weather="BB," the user 150 moves on foot from a user's home 1401 to a station 1402 on a route indicated by an arrow 1411.

In this case, at an intersection 1403, the user 150 shakes his/her head from side to side in order to check both sides. In other words, at the intersection 1403, a state in which the side-to-side shaking angle θ is large is the stationary state for the user 150. Consequently, when recognizing that the user 150 has moved to the intersection 1403, the state change determining unit 410 refers to the state change determination information in which the standard information about the side-to-side shaking angle is θ2 (>θ1) to perform the state change determination processing.

At an intersection 1404 after walking up an uphill slope, the pulse rate P of the user 150 increases. In other words, at the intersection 1404, a state in which the pulse rate P is large is the stationary state for the user 150. Consequently, when recognizing that the user 150 has moved to the intersection 1404, the state change determining unit 410 refers to the state change determination information in which the standard information about the pulse rate is P3 (>P2) to perform the state change determination processing.

At an intersection 1405 having a signal, the travel speed V of the user 150 becomes zero. In other words, at the intersection 1405, the travel speed V=0 is the stationary state for the user 150. Consequently, when recognizing that the user 150 has moved to the intersection 1405, the state change determining unit 410 refers to the state change information defining no standard information about the travel speed V to perform the state change determination processing.

The user 150 who is walking along a road 1407 extending along a railway track 1406 sees a train traveling along the railway track 1406, whereby the focal length becomes long, and the time during which the sight line direction is constant becomes long. Consequently, when recognizing that the user 150 is walking along the road 1407, the state change determining unit 410 refers to the state change determination information in which the standard information about the focal length is L2 (>L1) and the standard information about the time during which the sight line direction is constant is T2 (>T1).

FIG. 15 is a diagram for illustrating the state change determination information when date and time="DD," weather="BB," and atmospheric temperature="CC." When it is assumed that date and time="DD" is what is called a going-home time zone, and when weather="BB," the user 150 moves on foot from the station 1402 to the user's home 1401 on a route indicated by an arrow 1511.

In this case, at a pedestrian crossing 1501 having a signal, the travel speed V of the user 150 becomes zero. In other words, at the pedestrian crossing 1501, the travel speed V=0 is the stationary state for the user 150. Consequently, when recognizing that the user 150 has moved to the pedestrian crossing 1501, the state change determining unit 410 refers to the state change determination information defining no standard information about the travel speed to perform the state change determination processing.

At the intersection 1403, the user 150 shakes his/her head from side to side in order to check both sides. In other words, at the intersection 1403, a state in which the side-to-side shaking angle θ is large is the stationary state for the user 150. Consequently, when recognizing that the user 150 has moved to the intersection 1403, the state change determining unit 410 refers to the state change determination information in which the standard information about the side-to-side shaking angle is θ2 (>θ1) to perform the state change determination processing.

FIG. 16 is a diagram for illustrating the state change determination information when date and time="AA," weather="FF," and atmospheric temperature="GG." Although date and time="AA" is what is called a commuting time zone similarly to the case in FIG. 14, when weather="FF," and atmospheric temperature="GG," the user 150 moves by bus from the user's home 1401 to the station 1402 on a route indicated by an arrow 1611.

In this case, at a bus stop 1601, the travel speed V of the user 150 becomes zero. The user 150 shakes his/her head from side to side in order to check the traffic of buses. In other words, at the bus stop 1601, a state in which the travel speed V is zero and the side-to-side shaking angle θ is large is the stationary state for the user 150. Consequently, when recognizing that the user 150 has moved to the bus stop 1601, the state change determining unit 410 refers to the state change determination information defining no standard information about the travel speed and in which the standard information about the side-to-side shaking angle is θ2 (>θ1).

After getting on a bus, the user 150 looks at a scenery outside the window. Consequently, as the focal length of the user 150 becomes large, the side-to-side shaking angle becomes large.

In other words, while the user 150 is moving along the route along the arrow 1611, a state in which the focal length is large and the side-to-side shaking angle is large is the stationary state for the user 150. Consequently, when recognizing that the user 150 is moving along the route along the arrow 1611, the state change determining unit 410 refers to the state change determination information in which the standard information about the focal length is L2 (>L1) and the standard information about the side-to-side shaking angle is θ2 (>θ1).

As described above, the sight line information collecting system, which is an example of the information processing system according to the present embodiment, is:

configured to prepare a plurality of pieces of state change determination information in advance in consideration of changing behavior patterns of the user in accordance with the situation such as date and time, weather, or atmospheric temperature and to refer to the state change determination information corresponding to the respective situations in which the user is present, thereby determining the presence or absence of the state change of the user.

Consequently, the sight line information collecting system, which is an example of the information processing system according to the present embodiment, can determine the state change of the user with high precision.

Other Embodiments

In the first to the third embodiments, when determining that the state of the user 150 has changed, the state change determining unit 410 or 1310 notifies the state change information transmitter 420 of the sight line direction data acquired from the sight line data analyzing unit 401. However, the sight line direction data that the state change information transmitter 420 is notified of may be sight line direction data calculated again based on the direction of a face identified based on the side-to-side shaking angle, the up-and-down shaking angle, or the like, the direction of the body of the user 150, or the like, for example.

Although the mobile terminal 120 includes the state change determining unit 410 in the first to the third embodiments, the present invention is not limited thereto, and the state change determining unit 410 may be included in the server apparatus 130, for example. The server apparatus 130 may include part of the functions other than the state change determining unit 410 that are described as being included in the mobile terminal 120.

In this case, the pieces of motion data detected by the mobile terminal are successively transmitted to the server apparatus 130, and the presence or absence of the state change of the user carrying the mobile terminal is determined by the server apparatus 130. This case can also reduce the amount of the pieces of motion data (the latitude data, the longitude data, the altitude data, the sight line direction data) used to identify the area in which the event is occurring and can thereby obtain advantageous effects similar to those of the first to the third embodiments.

Although the wearable device 110 and the mobile terminal 120 are separate, and the wearable device 110 and the mobile terminal 120 are connected via the short-range wireless communication in the first to the third embodiments, the embodiments is not limited thereto. The wearable device 110 may have the functions of the mobile terminal 120, and the wearable device 110 may directly communicate with the server apparatus 130, for example.

Although the wearable device 110 collectively transmits the pieces of motion data detected by the motion sensors included in the wearable device 110 to the mobile terminal 120 in the first to the third embodiments, the embodiments is not limited thereto. Motion sensors separate from the wearable device 110 may be mounted on the wearable device 110, and the individual motion sensors may perform the short-range wireless communication with the mobile terminal 120, for example.

In this case, the wearable device 110 functions as a tool for causing the user 150 to wear the motion sensors. The mobile terminal 120 includes an acquiring unit that directly acquires the pieces of motion data detected by the respective motion sensors.

Figure 17:
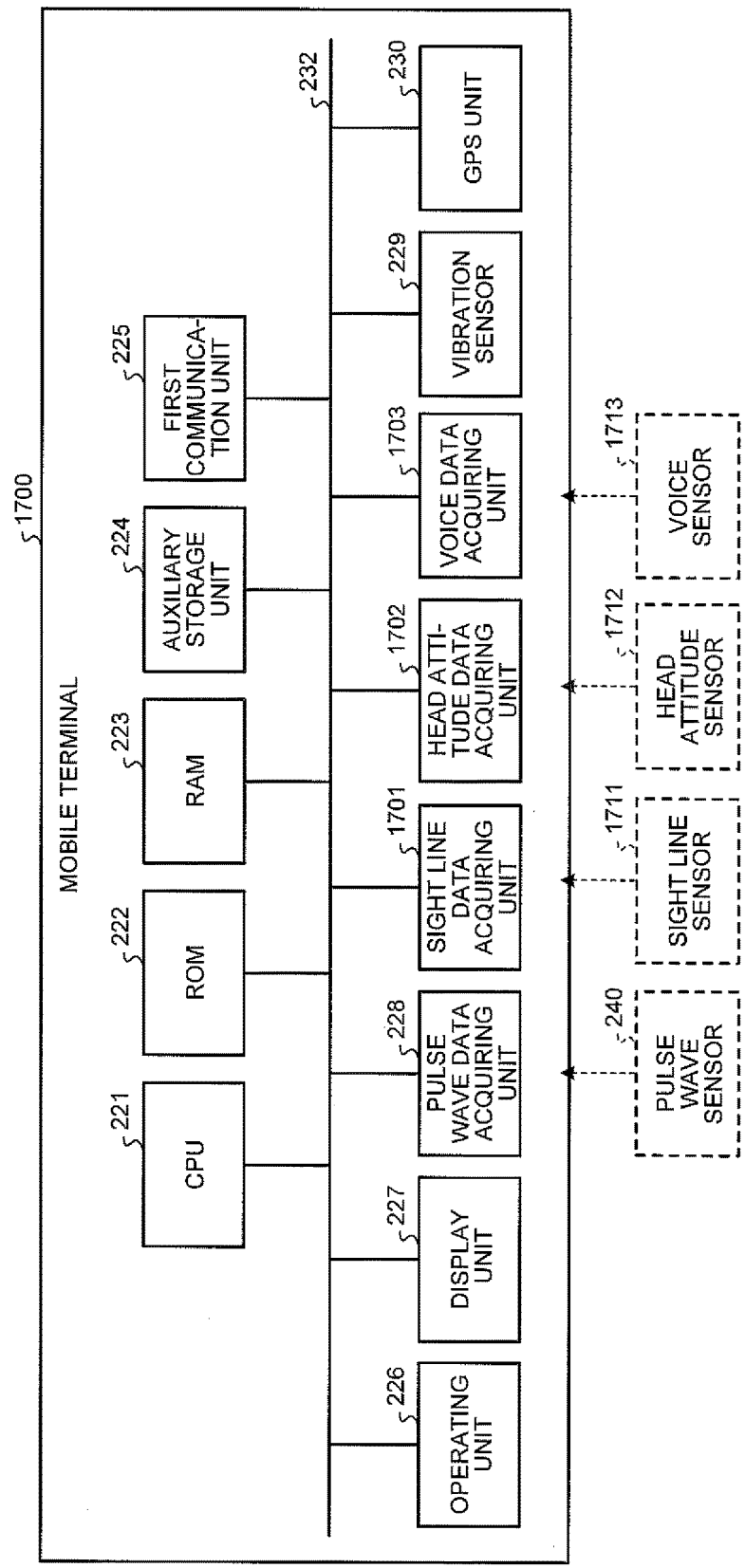
FIG. 17 is a diagram of an example of a hardware configuration of the mobile terminal.

FIG. 17 is a diagram of a hardware configuration of a mobile terminal having the acquiring unit that directly acquires the pieces of motion data. As illustrated in FIG. 17, this mobile terminal 1700 includes a sight line data acquiring unit 1701 that acquires sight line data detected by a sight line sensor 1711, in addition to the pulse wave data acquiring unit 228 that acquires the pulse wave data detected by the pulse wave sensor 240. Furthermore, the mobile terminal 1700 includes a head attitude data acquiring unit 1702 that acquires head attitude data detected by a head attitude sensor 1712 and a voice data acquiring unit 1703 that acquires voice data detected by a voice sensor 1713.

Although the first to the third embodiments do not refer to particular applications of the sight line information collecting system 100, examples of the applications of the sight line information collecting system 100 include the following, for example:

A Case in which an Abnormality is Occurring

When an abnormality is occurring (when a crack in the ground is occurring, a foreign object is getting caught on an electric wire, a foreign object is lying on a road, or the like), the sight line information collecting system 100 identifies an area in which any of these abnormalities has occurred and estimates and outputs what abnormality it is. Consequently, a service that immediately notifies a predetermined address corresponding to the type of the abnormality of the area in which the abnormality has occurred can be provided, for example.

A Case in which an Event Interesting People is Occurring

When an event interesting people is occurring (when digital signage is being displayed, fireworks are being launched, or the like), the sight line information collecting system 100 can calculate the number of people visually recognizing the event in identifying the area in which the event is occurring. Consequently, a service that evaluates the degree of attention of these events can be provided, for example.

A Case in which an Event Accompanied by Movement

When an event accompanied by movement is occurring (when an advertising car has passed by, an animal that escaped has crossed, or the like), the sight line information collecting system 100 can successively track changes in the position of the area in which any of these event is occurring. Consequently, a service that notifies the user of the area in which the event is occurring in real time can be provided, for example.

The embodiments are not limited to the configurations disclosed in this specification such as the configurations disclosed in the embodiments and combinations with other components. They can be altered without departing from the essence of the embodiments and can be determined as appropriate in accordance with how they are applied.

A system that identifies an area in which an event to which a plurality of people pay attention is occurring based on sight lines of the people can be achieved at low cost.

Although the invention has been described with respect to specific embodiments for a complete and clear disclosure, the appended claims are not to be thus limited but are to be construed as embodying all modifications and alternative constructions that may occur to one skilled in the art that fairly fall within the basic teaching herein set forth.

What is claimed is:

1. An information processing system comprising:
   a mobile terminal including:
      a motion sensor that detects motion information of the mobile terminal of a user; and
      a mobile terminal processor operatively coupled to the motion sensor, the mobile terminal processor being programmed to:
         receive and analyze sight line data detected by a wearable device worn by the user; and
         generate and transmit state change information based on the analyzed sight line data and the detected motion information; and
   a server including a server processor communicating with the mobile terminal, the server processor being programmed to:
      acquire the state change information from the mobile terminal indicating a current motion of the user;
      compare the acquired motion information with standard information indicating a motion of the user in a predetermined state to determine a motion state change of the user; and
      in response to determining that the motion state change is present, calculate an area that the user visually recognizes based on the sight line data concerning a sight line of the user and the detected motion information.

2. The information processing system according to claim 1, wherein the server processor is programmed to:
  in response to determining that a state change is present, collect the sight line data concerning the sight line of the user from the acquired motion information; and
  calculate the area that the user visually recognizes based on the collected sight line information.

3. The information processing system according to claim 2, wherein the server processor is programmed to calculate an area that a plurality of users visually recognizes in a duplicate manner based on collected pieces of sight line data of the plurality of users.

4. The information processing system according to claim 1, wherein the server processor is programmed to determine that the motion state change of the user is present when a focal length of an eye of the user is a predetermined threshold or more.

5. The information processing system according to claim 1, wherein the server processor is programmed to determine that the motion state change of the user is present when a time during which a sight line direction of an eye of the user is constant is a predetermined threshold or more.

6. The information processing system according to claim 1, wherein the server processor is programmed to determine that a state change of the user is present when a lateral shaking angle of the user is a predetermined threshold or more, or when an up-and-down shaking angle of the user is a predetermined threshold or more.

7. The information processing system according to claim 1, wherein:
  the standard information is managed separately in accordance with a parameter indicating a situation in which the user is present; and
  the server processor is programmed to compare the motion information with the standard information corresponding to a situation in which the user is currently present to determine a presence or absence of the motion state change of the user.

8. The information processing system according to claim 7, wherein:
  the parameter indicating the situation in which the user is present contains any of: date and time, position, weather, and atmospheric temperature, and
  the standard information in each situation is determined based on past behavior patterns of the user.

9. A mobile terminal connected to a server apparatus, the mobile terminal comprising:
  a motion sensor that detects motion information of the mobile terminal of a user; and
  a mobile terminal processor operatively coupled to the motion sensor, the mobile terminal processor being programmed to:
    receive and analyze sight line data detected by a wearable device worn by the user;
    generate state change information based on the analyzed sight line data and the detected motion information, the state change information indicating a current motion of the user;
    compare the motion information with standard information indicating a motion of the user in a predetermined state to determine a motion state change of the user; and
    in response to determining that the motion state change is present, transmit sight line data concerning a sight line of the user and the detected motion information to the server apparatus.

10. A server apparatus comprising:
  a server processor communicating with a mobile terminal, the server processor being programmed to:
    acquire state change information from the mobile terminal indicating a current motion of a user of the mobile terminal, the state change information being based on sight line data detected by a wearable device worn by the user and motion information detected by a motion sensor of the mobile terminal;
    compare the acquired motion information with standard information indicating a motion of the user in a predetermined state to determine a motion state change of the user; and
    in response to determining that the motion state change is present, calculate an area that the user visually recognizes based on the sight line data concerning a sight line of the user and the detected motion information.

11. A method for processing information, the method comprising:
  acquiring state change information from a mobile terminal of a user indicating a current motion of the user, the state change information being based on sight line data detected by a wearable device worn by the user and motion information detected by a motion sensor of the mobile terminal;
  comparing the acquired motion information with standard information indicating a motion of the user in a predetermined state to determine a motion state change of the user; and
  in response to determining that the motion state change is present, calculating an area that the user visually recognizes based on the sight line data concerning a sight line of the user and the detected motion information.

12. A non-transitory computer-readable storage medium having stored therein a computer program that causes a mobile terminal connected to a server apparatus to execute:
  receiving and analyzing sight line data detected by a wearable device worn by a user;
  generating state change information based on the analyzed sight line data and detected motion information detected by a motion sensor of the mobile terminal, the state change information indicating a current motion of a user;
  comparing the motion information with standard information indicating a motion of the user in a predetermined state to determine a motion state change of the user; and
  in response to determining that the motion state change is present, transmitting sight line data concerning a sight line of the user and the detected motion information to the server apparatus.

13. A non-transitory computer-readable storage medium having stored therein a computer program that causes a server apparatus to execute:
  acquiring state change information from a mobile terminal of a user indicating a current motion of a user carrying the mobile terminal, the state change information being based on sight line data detected by a wearable device worn by the user and motion information detected by a motion sensor of the mobile terminal;
  comparing the acquired motion information with standard information indicating a motion of the user in a predetermined state to determine a motion state change of the user; and
  in response to determining that the motion state change is present, calculating an area that the user visually recognizes based on the sight line data concerning a sight line of the user and the detected motion information.

* * * * *